(12) United States Patent
Wang et al.

(10) Patent No.: US 12,231,830 B2
(45) Date of Patent: Feb. 18, 2025

(54) SYSTEM AND METHOD FOR ANALYZING SURFACE FEATURES USING A LOW-DIMENSIONAL COLOR SPACE CAMERA

(71) Applicant: University of Washington, Seattle, WA (US)

(72) Inventors: Ruikang K. Wang, Seattle, WA (US); Qinghua He, Seattle, WA (US)

(73) Assignee: University of Washington, Seattle, WA (US)

( * ) Notice: Subject to any disclaimer, the term of this patent is extended or adjusted under 35 U.S.C. 154(b) by 217 days.

(21) Appl. No.: 17/765,317

(22) PCT Filed: Sep. 30, 2020

(86) PCT No.: PCT/US2020/053564
§ 371 (c)(1),
(2) Date: Mar. 30, 2022

(87) PCT Pub. No.: WO2021/067451
PCT Pub. Date: Apr. 8, 2021

(65) Prior Publication Data
US 2022/0329767 A1 Oct. 13, 2022

Related U.S. Application Data

(60) Provisional application No. 62/909,097, filed on Oct. 1, 2019.

(51) Int. Cl.
*H04N 9/67* (2023.01)
*A61B 5/00* (2006.01)
(Continued)

(52) U.S. Cl.
CPC ............ *H04N 9/67* (2013.01); *A61B 5/14546* (2013.01); *A61B 5/1455* (2013.01); *A61B 5/443* (2013.01);
(Continued)

(58) Field of Classification Search
None
See application file for complete search history.

(56) References Cited

U.S. PATENT DOCUMENTS

| 5,502,799 | A | 3/1996 | Tsuji |
| 9,474,506 | B2 | 10/2016 | Magnin |

(Continued)

FOREIGN PATENT DOCUMENTS

| WO | 9013091 A1 | 11/1990 |
| WO | 9837811 A1 | 9/1998 |

(Continued)

OTHER PUBLICATIONS

International Preliminary Report on Patentability mailed Apr. 5, 2022, issued in the corresponding International Application No. PCT/US2020/053564, filed Sep. 30, 2020, 8 pages.

(Continued)

*Primary Examiner* — Stefan Gadomski
(74) *Attorney, Agent, or Firm* — Christensen O'Connor Johnson Kindness PLLC

(57) ABSTRACT

In some embodiments, a computer-implemented method of generating a visualization of wavelength-dependent surface characteristics is provided. A computing device receives an input image captured by a camera, wherein the input image includes information in a low-dimensional color space. The computing device processes the input image to determine spectrum band information in a high-dimensional color space that corresponds to the input image. The computing device extracts subtractive information from the spectrum
(Continued)

band information to obtain wavelength-dependent surface characteristic information, The computing device generates the visualization using the wavelength-dependent surface characteristic information. In some embodiments, the computing device may be a smartphone.

19 Claims, 8 Drawing Sheets

(51) Int. Cl.
    *A61B 5/145* (2006.01)
    *A61B 5/1455* (2006.01)
    *G06T 7/00* (2017.01)
    *G06T 7/90* (2017.01)
    *H04N 17/00* (2006.01)
    *H04N 23/56* (2023.01)

(52) U.S. Cl.
    CPC .......... *A61B 5/4547* (2013.01); *A61B 5/6898* (2013.01); *G06T 7/0012* (2013.01); *G06T 7/90* (2017.01); *H04N 23/56* (2023.01); *G06T 2207/10024* (2013.01); *G06T 2207/10064* (2013.01); *G06T 2207/30036* (2013.01); *G06T 2207/30088* (2013.01); *G06T 2207/30201* (2013.01); *H04N 17/002* (2013.01)

(56) References Cited

U.S. PATENT DOCUMENTS

| | | | |
|---|---|---|---|
| 2008/0146918 | A1 | 6/2008 | Magnin |
| 2008/0278592 | A1* | 11/2008 | Kuno ............... H04N 23/11 348/E9.002 |
| 2009/0018422 | A1 | 1/2009 | Banet |
| 2013/0051827 | A1* | 2/2013 | Fukumuro ......... G03G 15/5058 399/49 |
| 2013/0289941 | A1* | 10/2013 | Keydar ............... H04N 1/6097 356/402 |
| 2014/0118736 | A1* | 5/2014 | Norris ................. G01N 21/25 702/191 |
| 2014/0195189 | A1* | 7/2014 | Norris ................. G01J 3/462 702/104 |
| 2016/0166150 | A1* | 6/2016 | Vilenskii ............ A61B 5/0077 348/77 |
| 2017/0347886 | A1 | 12/2017 | Tran |
| 2018/0255280 | A1* | 9/2018 | Gutierrez ............. G01S 17/32 |
| 2019/0200941 | A1 | 7/2019 | Chandran |
| 2019/0274619 | A1 | 9/2019 | Gareau et al. |
| 2019/0320875 | A1 | 10/2019 | Jones |
| 2021/0201479 | A1 | 7/2021 | Fan et al. |
| 2022/0240786 | A1 | 8/2022 | Subhash et al. |

FOREIGN PATENT DOCUMENTS

| | | |
|---|---|---|
| WO | 2011070357 A1 | 6/2011 |
| WO | 2016152900 A1 | 9/2016 |
| WO | 2017012675 A1 | 1/2017 |
| WO | 2022/003308 A1 | 1/2022 |

OTHER PUBLICATIONS

International Search Report and Written Opinion mailed Jan. 6, 2021, issued in the corresponding International Application No. PCT/US2020/053564, filed Sep. 30, 2020, 9 pages.
Achten, Juul, and Asker E. Jeukendrup. "Heart rate monitoring." Sports medicine 33.7 (2003): 517-538.
Basiri, Ali, et al. "Use of a multi-spectral camera in the characterization of skin wounds." Optics express 18.4 (2010): 3244-3257.
Benedetto, Simone, et al. "Assessment of the Fitbit Charge 2 for monitoring heart rate." PloS one 13.2 (2018): e0192691.

Chen, Xinlin, et al. "In vivo real-time imaging of cutaneous hemoglobin concentration, oxygen saturation, scattering properties, melanin content, and epidermal thickness with visible spatially modulated light." Biomedical optics express 8.12 (2017): 5468-5482.
Cheong, Wai-Fung, Scott A. Prahl, and Ashley J. Welch. "A review of the optical properties of biological tissues." IEEE journal of quantum electronics 26.12 (1990): 2166-2185.
Clancy, Neil T., et al. "Intraoperative measurement of bowel oxygen saturation using a multispectral imaging laparoscope." Biomedical optics express 6.10 (2015): 4179-4190.
Diaz, Keith M., et al. "Fitbit®: An accurate and reliable device for wireless physical activity tracking." International journal of cardiology 185 (2015): 1-5.
Diebele, Ilze, et al. "Clinical evaluation of melanomas and common nevi by spectral imaging." Biomedical optics express 3.3 (2012): 467-472.
Dugel, Pravin U., and Cheryl N. Zimmer. "Imaging of melanin disruption in age-related macular degeneration using multispectral imaging." Ophthalmic Surgery, Lasers and Imaging Retina 47.2 (2016): 134-141.
Fujiwara, Masaru, et al. "Spectroscopic imaging of blood vessels only near the skin surface for non-invasive blood glucose measurement." Proc. SPIE 9537, Clinical and Biomedical Spectroscopy and Imaging IV, 953714 (Jul. 15, 2015).
Gao, Liang, R. Theodore Smith, and Tomasz S. Tkaczyk. "Snapshot hyperspectral retinal camera with the Image Mapping Spectrometer (IMS)." Biomedical optics express 3.1 (2012): 48-54.
Ghassemi, Pejhman, et al. "A polarized multispectral imaging system for quantitative assessment of hypertrophic scars." Biomedical optics express 5.10 (2014): 3337-3354.
Goel, Mayank, et al. "HyperCam: hyperspectral imaging for ubiquitous computing applications." UbiComp 2015.
Hata, Ryuji, et al. "A reproducible model of middle cerebral artery occlusion in mice: hemodynamic, biochemical, and magnetic resonance imaging." Journal of Cerebral Blood Flow & Metabolism 18.4 (1998): 367-375.
Hirohara, Y., et al. "Development of fundus camera for spectral imaging using liquid crystal tunable filter." Investigative Ophthalmology & Visual Science 45.13 (2004): 2418-2418.
Jackson, James E., Averil O. Mansfield, and David J. Allison. "Treatment of high-flow vascular malformations by venous embolization aided by flow occlusion techniques." Cardiovascular and interventional radiology 19.5 (1996): 323-328.
Jakovels, Dainis, and Janis Spigulis. "2-D mapping of skin chromophores in the spectral range 500-700 nm." Journal of biophotonics 3.3 (2010): 125-129.
Kainerstorfer, Jana M., et al. "Principal component model of multispectral data for near real-time skin chromophore mapping." Journal of Biomedical Optics 15.4 (2010): 046007.
Kapsokalyvas, Dimitrios, et al. "Spectral morphological analysis of skin lesions with a polarization multispectral dermoscope." Optics express 21.4 (2013): 4826-4840.
Kellett, S. C., and D. J. Gawkrodger. "The psychological and emotional impact of acne and the effect of treatment with isotretinoin." British journal of Dermatology 140.2 (1999): 273-282.
Kim, Bumju, et al. "In vivo visualization of skin inflammation by optical coherence tomography and two-photon microscopy." Biomedical Optics Express 6.7 (2015): 2512-2521.
Kim, Sewoong, et al. "Smartphone-based multispectral imaging: system development and potential for mobile skin diagnosis." Biomedical optics express 7.12 (2016): 5294-5307.
Kuzmina, Ilona, et al. "Towards noncontact skin melanoma selection by multispectral imaging analysis." Journal of Biomedical optics 16.6 (2011): 060502.
Manson, Paul N., et al. "Improved survival in free skin flap transfers in rats." Surgery 99.2 (1986): 211-215.
Matthews, Thomas E., et al. "In vivo and ex vivo epi-mode pump-probe imaging of melanin and microvasculature." Biomedical optics express 2.6 (2011): 1576-1583.

(56) References Cited

OTHER PUBLICATIONS

Tanaka, Kenichi, et al. "Skin autofluorescence is associated with renal function and cardiovascular diseases in pre-dialysis chronic kidney disease patients." Nephrology Dialysis Transplantation 26.1 (2011): 214-220.
Nkengne, A., et al. "SpectraCam®: A new polarized hyperspectral imaging system for repeatable and reproducible in vivo skin quantification of melanin, total hemoglobin, and oxygen saturation." Skin Research and Technology 24.1 (2018): 99-107.
Pearson, Thomas C. "Hemorheologic considerations in the pathogenesis of vascular occlusive events in polycythemia vera." Seminars in thrombosis and hemostasis. vol. 23. No. 05. 1997.
Rehak, Jiri, and Matus Rehak. "Branch retinal vein occlusion: pathogenesis, visual prognosis, and treatment modalities." Current eye research 33.2 (2008): 111-131.
Penachini, M., et al. "Comparison of Polarfi RS800G3TM heart rate monitor with Polarfi S810iTM and electrocardiogram to obtain the series of RR intervals and analysis of heart rate variability at rest." Clin Physiol Funct Imaging (2016) 36, pp. 112-117.
Robles, Francisco E., Jesse W. Wilson, and Warren S. Warren. "Quantifying melanin spatial distribution using pump-probe microscopy and a 2-D morphological autocorrelation transformation for melanoma diagnosis." Journal of biomedical optics 18.12 (2013): 120502.
Rosen, Cheryl F., et al. "Immediate pigment darkening: visual and reflectance spectrophotometric analysis of action spectrum." Photochemistry and photobiology 51.5 (1990): 583-588.
Tseng, Sheng-Hao, et al. "Chromophore concentrations, absorption and scattering properties of human skin in-vivo." Optics express 17.17 (2009): 1-28.
Spigulis, Janis. "Multispectral, fluorescent and photoplethysmographic imaging for remote skin assessment." Sensors 17.5 (2017): 1165.
Spigulis, Janis, et al. "Smartphone snapshot mapping of skin chromophores under triple-wavelength laser illumination." Journal of Biomedical Optics 22.9 (2017): 091508.
Srivastava, Ruchir, et al. "Three-dimensional graph-based skin layer segmentation in optical coherence tomography images for roughness estimation." Biomedical Optics Express 9.8 (2018): 3590-3606.
Stamatas, Georgios N., and Nikiforos Kollias. "In vivo documentation of cutaneous inflammation using spectral imaging." Journal of Biomedical optics 12.5 (2007): 051603.
Tracy, C., et al. "Characterization of Renal Ischemia Using DLP Hyperspectral Imaging: A Pilot Study Comparing Artery-Only Occlusion Versus Artery and Vein Occlusion," Journal Of Endourology 24.3 (2010) 321-325.
Van Waateringe, Robert P., et al. "Skin autofluorescence predicts incident type 2 diabetes, cardiovascular disease and mortality in the general population." Diabetologia 62.2 (2019): 269-280.
Vasefi, Fartash, et al. "Polarization-sensitive hyperspectral imaging in vivo: a multimode dermoscope for skin analysis." Scientific reports 4.4924 (2014): 1-10.
Yaroslavsky, Anna N., Victor Neel, and R. Rox Anderson. "Demarcation of nonmelanoma skin cancer margins in thick excisions using multispectral polarized light imaging." Journal of investigative dermatology 121.2 (2003): 259-266.
Zhang, Rui-Lan, et al. "Temporal profile of ischemic tissue damage, neutrophil response, and vascular plugging following permanent and transient (2H) middle cerebral artery occlusion in the rat." Journal of the neurological sciences 125.1 (1994): 3-10.
Zonios, George, Julie Bykowski, and Nikiforos Kollias. "Skin melanin, hemoglobin, and light scattering properties can be quantitatively assessed in vivo using diffuse reflectance spectroscopy." Journal of Investigative Dermatology 117.6 (2001): 1452-1457.
He, et al., Hyperspectral imaging enabled by an unmodified smartphone for analyzing skin morphological features and monitoring hemodynamics, (Jan. 14, 2020), URL: https://opg.optica.org/boe/fulltext.cfm?uri=boe-11-2-895, (Apr. 13, 2022), XP055965074.
Jonghee Yoon, Joseph James, Waterhouse Dale J., Luthman A. Siri, Gordon George S. D., Di Pietro Massimiliano, Januszewicz Wladyslaw, Fitzgerald Rebecca C., Bohndiek Sarah E., "A clinically translatable hyperspectral endoscopy (HySE) system for imaging the gastrointestinal tract", Nature Communications, Nature Publishing Group, (Apr. 23, 2019), vol. 10, No. 1, doi:10.1038/s41467-019-09484-4, XP055650821.
Akhtar, N. and A. Mian, "Hyperspectral Recovery from RGB Images using Gaussian Processes," IEEE Transactions on Pattern Analysis and Machine Intelligence, vol. 42, No. 1, Jan. 2020.
Allen, J. "Photoplethysmography and its application in clinical physiological measurement," Physiol. Meas. 28 (2007) R1-R39; doi:10.1088/0967-3334/28/3/R01.
An, L. et al., "Ultrahigh sensitive optical microangiography for in vivo imaging of microcirculations within human skin tissue beds," Opt Express. Apr. 12, 2010; 18(8): 8220-8228.
Avci, MD, P. et al., "Low-level laser (light) therapy (LLLT) in skin: stimulating, healing, restoring," Semin Cutan Med Surg. Mar. 2013 ; 32(1): 41-52.
Baker, W. B. et al., "Modified Beer-Lambert law for blood flow," Biomedical Optics Express; Nov. 1, 2014; vol. 5, No. 11; DOI:10.1364/BOE.5.004053.
Bakermans, PhD, A. J. et al., "Dynamic Magnetic Resonance Measurements of Calf Muscle Oxygenation and Energy Metabolism in Peripheral Artery Disease," J. Magn. Reson. Imaging 2020;51:98-107.
Bal., U. "Non-contact estimation of heart rate and oxygen saturation using ambient light," Biomedical Optics Express; Jan. 1, 2015; vol. 6, No. 1; DOI:10.1364/BOE.6.000086; pp. 86-97.
Benaron, M.D., D. A. et al., "Continuous, Noninvasive, and Localized Microvascular Tissue Oximetry Using Visible Light Spectroscopy," Anesthesiology 2004; 100:1469-75.
C. A. Lewis, W. Fergusson, T. Eaton, I. Zeng, and J. Kolbe, "Isolated nocturnal desaturation in COPD: prevalence and impact on quality of life and sleep," Thorax 64(2), 133-138 (2009).
W. W. Flemons, D. Buysse, S. Redline, A. Oack, K. Strohl, J. Wheatley, T. Young, N. Douglas, P. Levy, W. McNicolas, J. Fleetham, D. White, W. Schmidt-Nowarra, D. Carley, and J. Romaniuk, "Sleep-related breathing disorders in adults: recommendations for syndrome definition and measurement techniques in clinical research. The Report of an American Academy of Sleep Medicine Task Force," Sleep 22(5), 667-689 (1999).
Thirumalaisamy P. Velavan, and Christian G. Meyer, "The COVID-19 epidemic," Tropical medicine & international health 25 (3), 278-280 (2020).
A. D. Pitkin, C. M. Roberts and J. A. Wedzicha, "Arterialised earlobe blood gas analysis: an underused technique," Thorax 49, 364-366(1994).
J. W. Severinghaus, P. Astrup, and J. F. Murray, "Blood Gas Analysis and Critical Care Medicine," American Journal of Respiratory and Critical Care Medicine 157(4), S114-S122 (1998).
J. W. Severinghaus and Y. Honda, "History of blood gas analysis. VII. Pulse oximetry," J. Clin. Monitor Comput. 3, 135-138 (1987).
Y. Sun, S. Hu, V. Azorin-Peris, R. Kalawsky, and S. Greenwald, "Noncontact imaging photoplethysmography to effectively access pulse rate variability," J. Biomed. Opt. 18(6), 061205 (2012).
L. Tarassenko, M. Villarroel, A. Guazzi, J. Jorge, D. A. Clifton, and C. Pugh, "Non-contact video-based vital sign monitoring using ambient light and auto-regressive models," Physiol. Meas. 35(5), 807-831 (2014).
D. Shao, Y. Yang, C. Liu, F. Tsow, H. Yu, and N. Tao, "Noncontact monitoring breathing pattern, exhalation flow rate and pulse transit time," IEEE Trans. Biomed. Eng. 61(11), 2760-2767 (2014).
A. Castillo, A. Sola, H. Baquero, F. Neira, R. Alvis, R. Deulofeut and A. Critz, "Pulse Oxygen Saturation Levels and Arterial Oxygen Tension Values in Newborns Receiving Oxygen Therapy in the Neonatal Intensive Care Unit: Is 85% to 93% an Acceptable Range?," Pediatrics 121(5), 882-889 (2008).
C. Guilleminault, S. J. Connolly and R. A. Winkle, "Cardiac arrhythmia and conduction disturbances during sleep in 400 patients with sleep apnea syndrome," The American Journal of Cardiology 52(5), 490-494(1983).

(56) References Cited

OTHER PUBLICATIONS

F. P. Wieringa, F. Mastik, and A. F. W. van der Steen, "Contactless Multiple Wavelength Photoplethysmographic Imaging: A First Step Toward "SpO2 Camera" Technology," Ann. Biomed. Eng. 33, 1034-1041 (2005).
K. Humphreys, T. Ward and C. Markham, "Noncontact simultaneous dual wavelength photoplethysmography: a further step toward noncontact pulse oximetry," Rev. Sci. Instrum. 78, 044304 (2007).
L. Kong, Y. Zhao, Y. Dong, Y. Jian, X. Jin, B. Li, Y. Feng, M. Liu, X. Liu, and H. Wu, "Non-contact detection of oxygen saturation based on visible light imaging device using ambient light," Opt. Express 21(15), 1764-1771 (2013).
I. Nishidate, K. Sasaoka, T. Yuasa, J. Niizeki, T. Maeda, and Y. Aizu, "Visualising of skin chromophore concentrations by use of RGB images," Opt. Lett. 33(19), 2263-2265 (2008).
D. F. Swinehart, "The Beer-Lambert Law", Journal of chemical education 39(7), 333-335 (1962).
I. Fine and A. Weinred, "Multiple-scattering effects in transmission oximetry," Med. Biol. Eng. Comput. 31, 516-522 (1993).
I. Fine and A. Weinred, "Multiple scattering effect in transmission pulse oximetry," Med. Biol. Eng. Comput. 33, 709-712 (1995).
A. R. Guazzi, M. Villarroel, J. Jorge, J. Daly, M. C. Frise, P. A. Robbins, and L. Tarassenko, "Non-contact measurement of oxygen saturation with an RGB camera," Biomed. Opt. Express 6, 3320-3338 (2015).
W. Karlen, G. Dumont, C. Petersen, J. Gow, J. Lim, J. Sleiman, and J. M. Ansermino, "Human-centered Phone Oximeter Interface Design for the Operating Room," Proceedings of the Int. Conf. on Health Informatics, 433-438 (2011).
F. Lamonaca, D. L. Carni, D. Grimaldi, A. Nastro, M. Riccio and V. Spagnolo, "Blood oxygen saturation measurement by smartphone camera," 2015 IEEE International Symposium on Medical Measurements and Applications (MeMeA) Proceedings, 359-364 (2015).
X. Ding, D. Nassehi and E. C. Larson, "Measuring Oxygen Saturation with Smartphone Cameras Using Convolutional Neural Networks," IEEE Journal of Biomedical and Health Informatics 23(6), 2603-2610 (2019).
Y. Shimada, I. Yoshiya, N. Oka and K. Hamaguri, "Effects of multiple scattering and peripheral circulation on arterial oxygen saturation measured with a pulse-type oximeter," Med. Biol. Eng. Comput. 22, 475-478 (1984).
M. H. Smith, "Optimum wavelength combinations for retinal vessel oximetry," Appl. Opt. 38, 258-67 (1999).
J. G. Webster, Design of Pulse Oximeters (CRC Press, Oxfordshire, United Kingdom, 1997).
G. Guven, M. P. Hilty, and C. Ince, "Microcirculation: physiology, pathophysiology, and clinical application," Blood purification 49, 143-150 (2020).
D. Lopez and C. M. Kramer, "Oxygenation and flow in the limbs: Novel methods to characterize peripheral artery disease," Current cardiovascular imaging reports 6, 150-157 (2013).
M. J. Sullivan, J. D. Knight, M. B. Higginbotham, and F. R. Cobb, "Relation between central and peripheral hemodynamics during exercise in patients with chronic heart failure. Muscle blood flow is reduced with maintenance of arterial perfusion pressure," Circulation 80, 769-781 (1989).
A. A. Frazier, T. J. Franks, T.-L. H. Mohammed, I. H. Ozbudak, and J. R. Galvin, "Pulmonary veno-occlusive disease and pulmonary capillary hemangiomatosis," Radiographics 27, 867-882 (2007).
H. M. A. Hofstee, A. V. Noordegraaf, A. E. Voskuyl, B. A. C. Dijkmans, P. E. Postmus, Y. M. Smulders, and E. H. Serné, "Nailfold capillary density is associated with the presence and severity of pulmonary arterial hypertension in systemic sclerosis," Annals of the rheumatic diseases 68, 191-195 (2009).
G. London, A. Covic, D. Goldsmith, A. Wiecek, G. Suleymanlar, A. Ortiz, Z. Massy, B. Lindholm, A. Martinez-Castelao, and D. Fliser, "Arterial aging and arterial disease: interplay between central hemodynamics, cardiac work, and organ flow-implications for CKD and cardiovascular disease," Kidney international supplements 1, 10-12 (2011).
L. Ostergaard, S. N. Jespersen, T. Engedahl, E. G. Jiménez, M. Ashkanian, M. B. Hansen, S. Eskildsen, and K. Mouridsen, "Capillary dysfunction: its detection and causative role in dementias and stroke," Current neurology and neuroscience reports 15, 37 (2015).
P. H. Tomlins and R. K. Wang, "Theory, developments and applications of optical coherence tomography," Journal of Physics D: Applied Physics 38, 2519-2535 (2005).
S. Eriksson, J. Nilsson, and C. Sturesson, "Non-invasive imaging of microcirculation: a technology review," Med Devices (Auckl) 7, 445-452 (2014).
J. Hansell, L. Henareh, S. Agewall, and M. Norman, "Non-invasive assessment of endothelial function—relation between vasodilatory responses in skin microcirculation and brachial artery," Clinical physiology and functional imaging 24, 317-322 (2004).
G. E. Gokcek, D. Kartal, N. Kalay, S. L. Çinar, G. Savaş, and M. Borlu, "The relationship between the severity of coronary artery disease and skin measurement parameters," Skin Research and Technology: Official Journal of International Society for Bioengineering and the Skin (ISBS)[and] International Society for Digital Imaging of Skin (ISDIS)[and] International Society for Skin Imaging (ISSI) (2020).
M. Ohmi, M. Kuwabara, and M. Haruna, "Dynamic imaging of a small artery underneath skin surface of a human finger by optical coherence tomography," (2013).
Q. He, T. Liu, and R. K. Wang, "Enhanced spatial resolution for snapshot hyperspectral imaging of blood perfusion and melanin information within human tissue," Journal of Biophotonics 13, e202000019 (2020).
V. Y. Toronov, X. Zhang, and A. G. Webb, "A spatial and temporal comparison of hemodynamic signals measured using optical and functional magnetic resonance imaging during activation in the human primary visual cortex," Neuroimage 34, 1136-1148 (2007).
C.-L. Chen and R. K. Wang, "Optical coherence tomography based angiography," Biomed. Opt. Express 8, 1056-1082 (2017).
International Search Report and Written Opinion mailed Feb. 28, 2024, issued in corresponding International Application No. PCT/US2023/077963, filed Oct. 26, 2023, 9 pages.
S. L. Davis, P. J. Fadel, J. Cui, G. D. Thomas, and C. G. Crandall, "Skin blood flow influences near-infrared spectroscopy-derived measurements of tissue oxygenation during heat stress," Journal of applied physiology 100, 221-224 (2006).
Z. Marcinkevics, U. Rubins, J. Zaharans, A. Miščuks, E. Urtane, and L. Ozolina-Moll, "Imaging photoplethysmography for clinical assessment of cutaneous microcirculation at two different depths," Journal of Biomedical Optics 21, 035005 (2016).
M. Paul, A. F. Mota, C. H. Antink, V. Blazek, and S. Leonhardt, "Modeling photoplethysmographic signals in camera-based perfusion measurements: optoelectronic skin phantom," Biomed. Opt. Express 10, 4353-4368 (2019).
T. Tamura, Y. Maeda, M. Sekine, and M. Yoshida, "Wearable photoplethysmographic sensors past and present," Electronics 3, 282-302 (2014).
D. Castaneda, A. Esparza, M. Ghamari, C. Soltanpur, and H. Nazeran, "A review on wearable photoplethysmography sensors and their potential future applications in health care," International journal of biosensors & bioelectronics 4, 195 (2018).
J. Liu, B. P.-Y. Yan, W.-X. Dai, X.-R. Ding, Y.-T. Zhang, and N. Zhao, "Multi-wavelength photoplethysmography method for skin arterial pulse extraction," Biomed. Opt. Express 7, 4313-4326 (2016).
A. A. R. Kamal, J. B. Harness, G. Irving, and A. J. Mearns, "Skin photoplethysmography a review," Computer methods and programs in biomedicine 28, 257-269 (1989).
D. Biswas, N. Simoes-Capela, C. Van Hoof, and N. Van Helleputte, "Heart rate estimation from wrist-worn photoplethysmography: A review," IEEE Sensors Journal 19, 6560-6570 (2019).
N. Paradkar and S. R. Chowdhury, "Cardiac arrhythmia detection using photoplethysmography," in IEEE, 113-116.
O. S. Hoilett, A. M. Twibell, R. Srivastava, and J. C. Linnes, "Kick LL: A smartwatch for monitoring respiration and heart rate using photoplethysmography," in (IEEE, 3821-3824.

(56) References Cited

OTHER PUBLICATIONS

M. van Gastel, S. Stuijk, and G. de Haan, "Robust respiration detection from remote photoplethysmography," Biomed. Opt. Express 7, 4941-4957 (2016).
V. V. Zaytsev, S. V. Miridonov, O. V. Mamontov, and A. A. Kamshilin, "Contactless monitoring of the blood-flow changes in upper limbs," Biomed. Opt. Express 9, 5387-5399 (2018).
W. Wang, A. C. den Brinker, and G. De Haan, "Full video pulse extraction," Biomed. Opt. Express 9, 3898-3914 (2018).
W. W. Muir and M. L. Wellman, "Hemoglobin solutions and tissue oxygenation," Journal of veterinary internal medicine 17, 127-135 (2003).
D. A. Low, H. Jones, N. T. Cable, L. M. Alexander, and W. L. Kenney, "Historical reviews of the assessment of human cardiovascular function: interrogation and understanding of the control of skin blood flow," European journal of applied physiology 120, 1-16 (2020).
M. Hellmann, M. Roustit, and J. L. Cracowski, "Skin microvascular endothelial function as a biomarker in cardiovascular diseases?," Pharmacological Reports 67, 803-810 (2015).
Q. He and R. Wang, "Hyperspectral imaging enabled by an unmodified smartphone for analyzing skin morphological features and monitoring hemodynamics," Biomed. Opt. Express 11, 895-910 (2020).
Q. He and R. K. Wang, "Analysis of skin morphological features and real-time monitoring using snapshot hyperspectral imaging," Biomed. Opt. Express 10, 5625-5638 (2019).
Q. He, Z. Sun, Y. Li, W. Wang, and R. K. Wang, "Smartphone-enabled snapshot multispectral autofluorescence imaging and its application for bacteria assessments in skin and oral cavity," Optics and Lasers in Engineering 140, 106546 (2021).
J. Eckhard, T. Eckhard, E. M. Valero, J. L. Nieves, and E. G. Contreras, "Outdoor scene reflectance measurements using a Bragg-grating-based hyperspectral imager," Applied Optics 54, D15-D24 (2015).
J. Hernandez-Andres, J. Romero, and R. L. Lee, "Colorimetric and spectroradiometric characteristics of narrow-field-of-view clear skylight in Granada, Spain," JOSA A 18, 412-420 (2001).
W. Karlen, J. Lim, J. M. Ansermino, G. Dumont, and C. Scheffer, "Design challenges for camera oximetry on a mobile phone," in 2012 Annual International Conference of the IEEE Engineering in Medicine and Biology Society, 2012), 2448-2451.
R. D. Muir, S. Z. Sullivan, R. A. Oglesbee, and G. J. Simpson, "Synchronous digitization for high dynamic range lock-in amplification in beam-scanning microscopy," Review of Scientific Instruments 85, 033703 (2014).
A. A. Kamshilin, S. Miridonov, V. Teplov, R. Saarenheimo, and E. Nippolainen, "Photoplethysmographic imaging of high spatial resolution," Biomed. Opt. Express 2, 996-1006 (2011).
K. Jackman and C. Iadecola, "Neurovascular regulation in the ischemic brain," Antioxidants & redox signaling 22, 149-160 (2015).
HH. Billett. "Hemoglobin and Hematocrit." in Clinical Methods: The History, Physical, and Laboratory Examinations. (Boston: Butterworths, 1990), Chap. 151.
P. Oltulu, B. Ince, N. Kokbudak, S. Findik, and F. Kilinc, "Measurement of epidermis, dermis, and total skin thicknesses from six different body regions with a new ethical histometric technique," Turkish Journal of Plastic Surgery 26, 56-61 (2018).
L. Wang, S. L. Jacques, and L. Zheng, "MCML—Monte Carlo modeling of light transport in multi-layered tissues," Computer methods and programs in biomedicine 47, 131-146 (1995).
R. K. Wang, "Signal degradation by multiple scattering in optical coherence tomography of dense tissue: a Monte Carlo study towards optical clearing of biotissues," Physics in Medicine & Biology 47, 2281 (2002).
S. L. Jacques, "Optical properties of biological tissues: a review," Physics in Medicine & Biology 58, R37 (2013).
J. Lee, M. Kim, H.-K. Park, and I. Y. Kim, "Motion Artifact Reduction in Wearable Photoplethysmography Based on Multi-Channel Sensors with Multiple Wavelengths," Sensors 20, 1493 (2020).
C.-C. Chang, C.-T. Wu, B. I. Choi, and T.-J. Fang, "MW-PPG sensor: An on-chip spectrometer approach," Sensors 19, 3698 (2019).
F. P. Wieringa, F. Mastik, and A. F. W. van der Steen, "Contactless multiple wavelength photoplethysmographic imaging: A first step toward "SpO 2 camera" technology," Annals of biomedical engineering 33, 1034-1041 (2005).
J. Zheng, S. Hu, V. Azorin-Peris, A. Echiadis, V. Chouliaras, and R. Summers, "Remote simultaneous dual wavelength imaging photoplethysmography: a further step towards 3-D mapping of skin blood microcirculation," in (International Society for Optics and Photonics, 68500S.
Janis Spigulis—non-patent publication, May 2017—Multispectral, Fluorescent and Photoplethysmographic Imaging for Remote Skin Assessment.
Zaunseder et al.—non-patent publication, Jun. 2018—Cardiovascular Assessment by Imaging Photoplethysmography.
Spigulis—non-patent publication, Aug. 2017—In vivo skin imaging prototypes "made in Latvia".
Pan & Shen—non-patent publication, Apr. 2019—Multispectral Image Super-Resolution via RGB Image Fusion and Radiometric Calibration.
T. B. Fitzpatrick, "Soleil et peau," J. de Medecine Esthetique 2, 33-34 (1975).
J. M. Bland and D. G. Altman, "Statistical methods for assessing agreement between two methods of clinical measurement," Lancet 327(8476), 307-310 (1986).
Michael W Browne, "Cross-Validation Methods," Journal of Mathematical Psychology 44 (1), 108-132 (2000).
Richard R. Picard and R. Dennis Cook, "Cross-Validation of Regression Models," Journal of the American Statistical Association 79 (387), 575-583(1984).
G. Zonios, J. Bykowski, and N. Kollias, "Skin melanin, hemoglobin, and light scattering roperties can be quantitatively assessed in vivo using diffuse reflectance spectroscopy," J. Invest. Dermatol. 117(6), 1452-1457 (2001).
S. Kwon, H. Kim and K. S. Park, "Validation of heart rate extraction using video imaging on a built-in camera system of a smartphone," Annual International Conference of the IEEE Engineering in Medicine and Biology Society, 2174-2177 (2012).
T.B. Plante, B. Urrea, Z.T. MacFarlane, R.S. Blumenthal, E.R. Miller, L.J. Appel and S.S. Martin, "Validation of the Instant Blood Pressure Smartphone App," JAMA Intern Med. 176(5):700-702 (2016).
J. W. Severinghaus, "Discovery of pulse oximetry," Anesth. Analg. 105(6), S1-S4 (2007).
Yoon, J. et al., "A clinically translatable hyperspectral endoscopy (HySE) system for imaging the gastrointestinal tract," Nature Commubications; (2019) 10:1902; https://doi.org/10.1038/s41467-019-09484-4; pp. 1-13.

* cited by examiner

SYSTEM AND METHOD FOR ANALYZING SURFACE FEATURES USING A LOW-DIMENSIONAL COLOR SPACE CAMERA

CROSS-REFERENCE(S) TO RELATED APPLICATION(S)

This application claims priority to Provisional Application No. 62/909,097, filed Oct. 1, 2019, the entire disclosure of which is hereby incorporated by reference herein for all purposes.

BACKGROUND

The application of hyperspectral imaging in cosmetology, dermatology, and dentistry is becoming increasingly popular and appealing to academic researchers and industrial entrepreneurs. Based on specific spectral characteristics of chromophores and fluorophores within body tissue, for example hemoglobin, melanin, and residing bacteria, hyperspectral imaging can be used to separate and contrast the target chromophores and fluorophores from others, upon which to analyze and monitor tissue features and status.

A number of hyperspectral imaging systems have been recently developed for the analysis of skin features. One of such uses monochromatic lasers or optical filters (either filter wheels or tunable filters) to provide specific spectral illumination and uses a single array detector to sequentially capture the tissue reflection or fluorescence images. For example, Kim et al. used LEDs to provide illumination in multispectral imaging. Diebele et al. tuned illumination wavelengths with liquid crystal filters for the clinical evaluation of melanomas and common nevi. In these devices, the wavelength-selection procedure requires at least tens of milliseconds to complete, leading to asynchronous data acquisitions for different wavelengths. Consequently, both tissue motion and device movements would inevitably cause motion artifacts, affecting the ability to interpret the final results. In addition, the need to select the wavelengths complicates the system setup, not a cost-effective solution for daily-use purposes.

Recent development of hyperspectral cameras surges new interests and new opportunities for hyperspectral imaging. This type of camera is manufactured by assembling an optical-filter array on the sensor, so that the pixels on the sensor can be separated into various wavebands, enabling spectral images across a wide spectrum to be captured at once. Such capability of snapshot-capturing hyperspectral images eliminates motion artifacts during data acquisition and improves device compactness. However, due to the complicated design and enabling fabrication, the cost of hyperspectral cameras is currently at least inhibitive for routine and cost-effective applications. Also, the number of pixels available in the spectral array of hyperspectral cameras is limited, which directly translates to the limited imaging resolution that can be achieved. As a result, a high demand remains for a system that is capable of high-resolution, hyperspectral imaging, and at the same time, is immune to motion artifacts, compact, and cost effective so that it can be deployed to a wider user community for daily assessment of the body tissue features, for example skin features.

In the past decade, developments in smartphones have changed the daily life of human beings. Both the technical development and the consumer group have experienced explosive improvements. Currently, a typical camera in a smartphone has 8 to 12 million pixels and is capable of high-speed imaging, making smartphones ideal as a low-cost and handy imaging devices for body tissue assessments.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In some embodiments, a computer-implemented method of generating a visualization of wavelength-dependent surface characteristics is provided. A computing device receives an input image captured by a camera, wherein the input image includes information in a low-dimensional color space. The computing device processes the input image to determine spectrum band information in a high-dimensional color space that corresponds to the input image. The computing device extracts subtractive information from the spectrum band information to obtain wavelength-dependent surface characteristic information. The computing device generates the visualization using the wavelength-dependent surface characteristic information.

In some embodiments, the low-dimensional color space has three spectrum bands. In some embodiments, the low-dimensional color space is a red-green-blue (RGB) color space. In some embodiments, the high-dimensional color space includes more than three spectrum bands.

In some embodiments, processing the input image to determine spectrum band information in the high-dimensional color space that corresponds to the input image includes transforming the information in the low-dimensional color space into the information in the high-dimensional color space using a transformation matrix. In some embodiments, the transformation matrix is a Wiener estimation matrix. In some embodiments, the transformation matrix is determined by capturing a calibration image of a color chart using a camera that matches the camera used to capture the input image, and using the calibration image and color reference information associated with the color chart to determine the transformation matrix.

In some embodiments, the color chart includes colors from 400 nm to 720 nm. In some embodiments, the transformation matrix is further determined by illuminating the color chart using an illumination source having a spectral power distribution that matches a spectral power distribution of an illumination source used while capturing the calibration image.

In some embodiments, the transformation matrix is further determined by capturing a reference image of the color chart using a high-dimensional color space camera, and determining the color reference information using the reference image. In some embodiments, the transformation matrix is further determined by determining the color reference information using a spectrometer.

In some embodiments, extracting information includes multiplying a detected reflectance by a ratio that represents a proportion of reflectance caused by a target characteristic and a background characteristic in a first set of wavelength bands compared to a second set of wavelength bands. In some embodiments, the target characteristic is melanin concentration, the background characteristic is hemoglobin concentration, and generating the visualization using the wavelength-dependent surface characteristic information includes generating a visualization of melanin concentration. In some embodiments, the target characteristic is hemoglobin concentration, the background characteristic is melanin concentration, and generating the visualization using the wavelength-dependent surface characteristic information includes generating a visualization of hemoglobin concentration. In some embodiments, the target characteristic is autofluorescence of bacteria-produced porphyrins, the background characteristic is autofluorescence of facial skin or teeth, and generating the visualization using the wavelength-dependent surface characteristic information includes generating a visualization of bacteria-produced porphyrins.

In some embodiments, a system is provided comprising a low-dimensional color space camera; an illumination source; and a non-transitory computer-readable medium. The computer-readable medium has computer-executable instructions stored thereon that, in response to execution by one or more processors of the system, cause the system to perform actions comprising: illuminating a target surface using the illumination source; capturing an input image of the target surface using the low-dimensional color space camera; processing the input image to determine spectrum band information in a high-dimensional color space that corresponds to the input image; extracting subtractive information from the spectrum band information to obtain wavelength-dependent surface characteristic information; and generating a visualization of a wavelength-dependent surface characteristic using the wavelength-dependent surface characteristic information.

In some embodiments, the system further comprises a smartphone that includes at least the low-dimensional color space camera and the illumination source.

In some embodiments, the low-dimensional color space camera is configured to capture images with information in three spectrum bands. In some embodiments, the three spectrum bands are a red band, a green and, and a blue band.

In some embodiments, processing the input image to determine spectrum band information in a high-dimensional color space that corresponds to the input image includes determining spectrum band information in more than three spectrum bands.

In some embodiments, processing the input image to determine spectrum band information in the high-dimensional color space that corresponds to the input image includes transforming the input image from the low-dimensional color space to the high-dimensional color space using a transformation matrix. In some embodiments, the transformation matrix is a Wiener estimation matrix. In some embodiments, the transformation matrix is determined by capturing a calibration image of a color chart using a calibration camera that matches the camera, and using the calibration image and color reference information associated with the color chart to determine the transformation matrix.

In some embodiments, the color chart includes colors from 400 nm to 720 nm. In some embodiments, the transformation matrix is further determined by illuminating the color chart using a calibration illumination source having a spectral power distribution that matches a spectral power distribution of the illumination source. In some embodiments, the transformation matrix is further determined by capturing a reference image of the color chart using a high-dimensional color space camera; and determining the color reference information using the reference image. In some embodiments, the transformation matrix is further determined by determining the color reference information using a spectrometer.

In some embodiments, extracting subtractive information from the spectrum band information to obtain wavelength-dependent surface characteristic information includes multiplying a detected reflectance by a ratio that represents a proportion of reflectance caused by a target characteristic and a background characteristic in a first set of wavelength bands compared to a second set of wavelength bands. In some embodiments, the target characteristic is melanin concentration, the background characteristic is hemoglobin concentration, and generating the visualization using the wavelength-dependent surface characteristic information includes generating a visualization of melanin concentration. In some embodiments, the target characteristic is hemoglobin concentration, the background characteristic is melanin concentration, and generating the visualization using the wavelength-dependent surface characteristic information includes generating a visualization of hemoglobin concentration. In some embodiments, the target characteristic is autofluorescence of bacteria-produced porphyrins, the background characteristic is autofluorescence of facial skin or teeth, and generating the visualization using the wavelength-dependent surface characteristic information includes generating a visualization of bacteria-produced porphyrins.

In some embodiments, a non-transitory computer-readable medium having computer-executable instructions stored thereon is provided. The instructions, in response to execution by one or more processors of a computing device, cause the computing device to perform any of the embodiments of a method as described above. In some embodiments, a computing device configured to perform any of the embodiments of a method as described above is provided.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
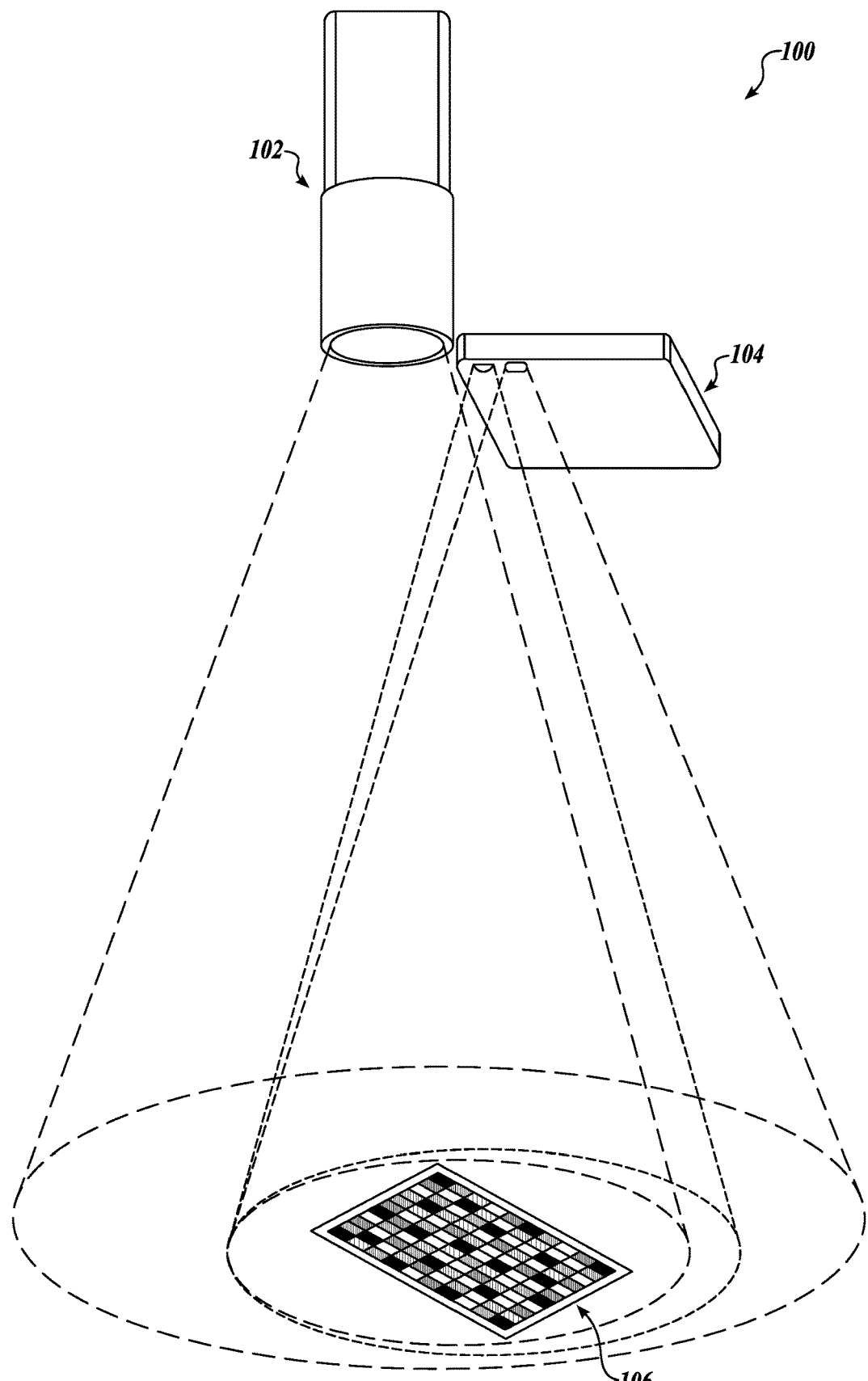
FIG. 1 is a schematic drawing that illustrates some components of a non-limiting example embodiment of a system for calibrating a device with a low-dimensional color space camera to generate pseudo-high-dimensional color space information according to various aspects of the present disclosure.

Chromophores and fluorophores, mainly hemoglobin, melanin, and residing bacteria, in the skin tissue are factors which have potential impacts on the skin assessments, both in clinical dermatology and cosmetics. Hemoglobin concentration is related to features including but not limited to skin redness, inflammations and vascular abnormalities. Melanin variation often presents in skin pigmentations, nevus and some skin cancers. Typical bacteria that reside in the skin, including but not limited to *Cutibacterium acnes*, are usually active in sebaceous glands. The relevant metabolic activities of these bacteria trigger risk of inflammation, leading to skin disorders such as folliculitis and acne vulgaris. Another common site of bacterial reproduction is within the oral cavity, potentially causing dental plaque that may progress to tooth decay, and further to periodontal diseases. Due to different optical properties, spectroscopic analysis is sometimes used in the quantitative measurements of these chromophores and fluorophores. Hyperspectral imaging provides a strategy with both spectral analysis and snapshot visualization abilities, which has shown the attractive potential to be more widely used in skin assessments. This is also true in the assessment of ocular tissue, ear tissue, and the oral cavity. There also may have interesting applications in the open surgery where the blood perfusion and chromophore/fluorophore concentrations within the exposed organs are often desired information to plan steps of surgical procedures.

Embodiments of systems and methods to use images captured by a low-dimensional color space camera (including but not limited to an RGB camera, such as an RGB camera of a smartphone) to provide hyperspectral information are presented herein. Since an RGB image lacks enough wavebands and spectral resolutions to properly conduct hyperspectral analysis, a transformation matrix may be applied to transform RGB images into hyperspectral images. Wiener estimation may provide accurate and high-resolution hyperspectral reconstruction.

The creation of a suitable transformation matrix may be conducted by the use of high resolution spectrometers. However, this type of calibration process uses an extremely high workload and perhaps instabilities because it has to be done at each wavelength one by one. Alternatively, in some embodiments of the present disclosure, a different training strategy may be used that lowers the workload: a state-of-the-art snapshot hyperspectral camera with 16 wavebands ranging from 470 nm to 720 nm may provide spectral reflection calibration. With the snapshot hyperspectral camera, the measurements of multiple wavelengths, multiple samples, and the co-registration of sampling area in each sample may be achieved without the high workload by selecting and calculating corresponding areas of the color chart in the RGB and hyperspectral images. The calibration may be performed by taking RGB and hyperspectral images of the color chart under the same illumination, reducing the workload in the process and increasing the stability of calibration.

In some embodiments of the present disclosure, the calibration process results in the construction of a Wiener estimation matrix that is applied to transform RGB images into hyperspectral images. Since the transformation may be done pixel by pixel, the reconstructed hyperspectral images may possess the same spatial pixel resolution as the original RGB images (typically around 800 million spatial pixels), and each pixel bearing spectral information with 16 wavebands in visible range. With weighted subtractions between different wavebands, the target chromophores may be contrasted from surrounding tissues.

Coupling with above hyperspectral reconstruction and post-processing steps, the smartphone camera's abilities to visualize blood, melanin absorption maps and oxygen saturation in the facial skin were tested. Compared with conventional hyperspectral imaging systems, which mostly rely on lasers or tunable optical filters, the smartphone-based hyperspectral imaging system eliminates the internal time difference within frames, greatly improving the imaging speed and immunity to motion artifacts. Furthermore, compared with advanced and costly hyperspectral cameras, the smartphone-based hyperspectral imaging disclosed herein is superior in terms of its spatial resolution. In addition, embodiments of the system and method show flexibility in terms of different illumination conditions. Embodiments of the present disclosure do not require any modification or addition to the existing hardware of smartphones, which makes hyperspectral imaging and analysis of skin tissue possible in daily scenes outside of controlled lab environments. This may be particularly important and appealing for the inhabitant regions where the resource-settings are relatively low.

Embodiments of the present disclosure may also apply to facilitate the diagnosis and prognosis of some other dermatosis with chromophore abnormalities, like malignant melanoma. In addition, the smartphone-based operation would hold the enormous promises in cosmetic applications, where the assessments of the UV spots and the skin hyperpigmentation are often desired. Embodiments of the system and method were further noted, with the extraction and separation of chromophores, to provide an ability of smartphone-based systems to quantitatively analyze and monitor skin temporal activities.

Embodiments of the present disclosure may also apply to facilitate the detection and analysis of fluorophore-producing bacteria when illuminated with a short-wavelength illumination source to cause autofluorescence. The presence of bacteria may be used to predict or diagnose various skin disorders, and/or may be used to predict or diagnose the formation of undesirable dental plaques.

As mentioned above, a transformation matrix can be used in order to obtain high-dimensional color space information from an image that contains low-dimensional color space information. For example, a transformation matrix can be determined that can extract information from more than three color bands from image information limited to three color bands (such as red-green-blue (RGB) information). In order to use such a transformation matrix, it is first determined using a calibration process. Traditionally, a calibration process includes measuring spectral reflection from color blocks with a well-characterized spectrometer. The sampling areas in the images taken by low-dimensional color space camera and the spectral reflection measurements need to match with each other, which is termed the co-registration step. While this is a viable approach, it increases the workload and introduces additional instabilities in the calibration. Furthermore, it requires performing the reflection measurement and co-registration at each color sample for all of the color samples, which may cause even heavier workloads and more instabilities.

In some embodiments, a snapshot hyperspectral camera may be used to mitigate the tedious procedures when using spectrometer for calibration. FIG. 1 is a schematic drawing that illustrates some components of a non-limiting example embodiment of such a system for calibrating a device with a low-dimensional color space camera to generate pseudo-high-dimensional color space information according to various aspects of the present disclosure.

As shown, the calibration system 100 includes a high-dimensional color space camera 102, a computing device 104, and a color chart 106. The color chart 106 is illuminated by an illumination source, a reference image of the color chart 106 is captured by the high-dimensional color space camera 102, and a calibration image of the color chart 106 is captured by a low-dimensional color space camera of the computing device 104.

In some embodiments, the high-dimensional color space camera 102 is any camera capable of capturing images in a high-dimensional color space. As used herein, the term "high-dimensional color space" refers to color information that is divided into more than three spectral channels, color bands, or wavelength bands, and the term "high-dimensional color space" may be used interchangeably with the term "hyperspectral". One non-limiting example of a high-dimensional color space camera 102 is a MQ022HG-IM-SM4X4-VIS, from XIMEA, Germany, with 16 spectral channels. By using a high-dimensional color space camera 102, many of the training steps that would be used if a spectrometer were being used are replaced by taking one low-dimensional color space image with the computing device 104 and one high-dimensional color space image of the color chart 106. One non-limiting example of a device suitable for use as a high-dimensional color space camera 102 in the calibration system 100 is a MQ022HG-IM-SM4X4-VIS, made by XIMEA, Germany. This device houses a CMOS sensor with 2048×1088 pixels, where a filter array separates the sensor array into 512×272 super-pixels. Each super-pixel contains a 4×4 spectral sensitive pixel-matrix that are sensitive to 16 wavebands.

In some embodiments, the computing device 104 includes a low-dimensional color space camera, which is used to capture an image of the color chart 106 in the low-dimensional color space. As used herein, the term "low-dimensional color space" refers to color information that is divided into three spectral channels, color bands, or wavelength bands, and the term "RGB" may be used interchangeably with the term "low-dimensional." Though a red-green-blue (RGB) color space is discussed primarily herein as the low-dimensional color space, one will note that other low-dimensional color spaces may be used without departing from the scope of the present disclosure. For example, instead of an RGB color space, some embodiments of the present disclosure may use a CMYK color space, a YIQ color space, a YPbPr color space, a YCbCr color space, an HSV color space, an HSL color space, a TSL color space, a CIEXYZ color space, an sRGB color space, an L*A*B color space, or an ICtCp color space.

In some embodiments, the computing device 104 includes the low-dimensional color space camera, the illumination source, and processing elements to be used for calibration as discussed below. In some such embodiments, the computing device 104 may be a smartphone or other device that includes all of these elements. In some embodiments, the low-dimensional color space camera, the illumination source, and/or the processing elements may be provided in separate devices. Importantly, the illumination source and low-dimensional color space camera used during calibration should match the illumination source and low-dimensional color space camera used during visualization generation or other processes. To match, in some embodiments the illumination source used during visualization generation may be the same device as the illumination source used during calibration, and the low-dimensional color space camera used during visualization may be the same device as the low-dimensional color space camera used during calibration. In some embodiments, matching devices may be different devices with matching performance characteristics. For example, the illumination source may be a flashlight of a smartphone, and matching devices may be different smartphones of the same model (which would have the same model flashlight with the same spectral characteristics). As another example, the illumination source may be a camera of a smartphone, and matching devices may again be different smartphones of the same model (which would have the same resolution and spectral performance characteristics).

In some embodiments, the color chart 106 includes a plurality of different colors to be imaged by the high-dimensional color space camera 102 and the computing device 104. In some embodiments, the color chart 106 may include 100 different colors spaced throughout a visible spectrum using any suitable technique, including but not limited to being randomly spaced and being evenly spaced. In some embodiments, a smaller or greater number of colors may be used. In some embodiments, the color chart 106 may also include a portion from which spectral characteristics of the illumination source may be determined. As a non-limiting example, the color chart 106 may include a polymer white diffuser standard, such as a standard of 95% reflectance manufactured by SphereOptics GmbH. In some embodiments, such a standard from which spectral characteristics of the illumination source may be separate from the color chart 106.

In some embodiments, the wavelength information may be obtained from the color chart 106 using some other technique, including but not limited to measurement by a spectrometer. In some embodiments, the color chart 106 may include colors that represent known values (that is, the wavelength information associated with each color block is known). In such embodiments, capturing the reference image may be skipped, and the known values for the color chart 106 may be used to calibrate the computing device 104 as descried below.

Figure 2B:
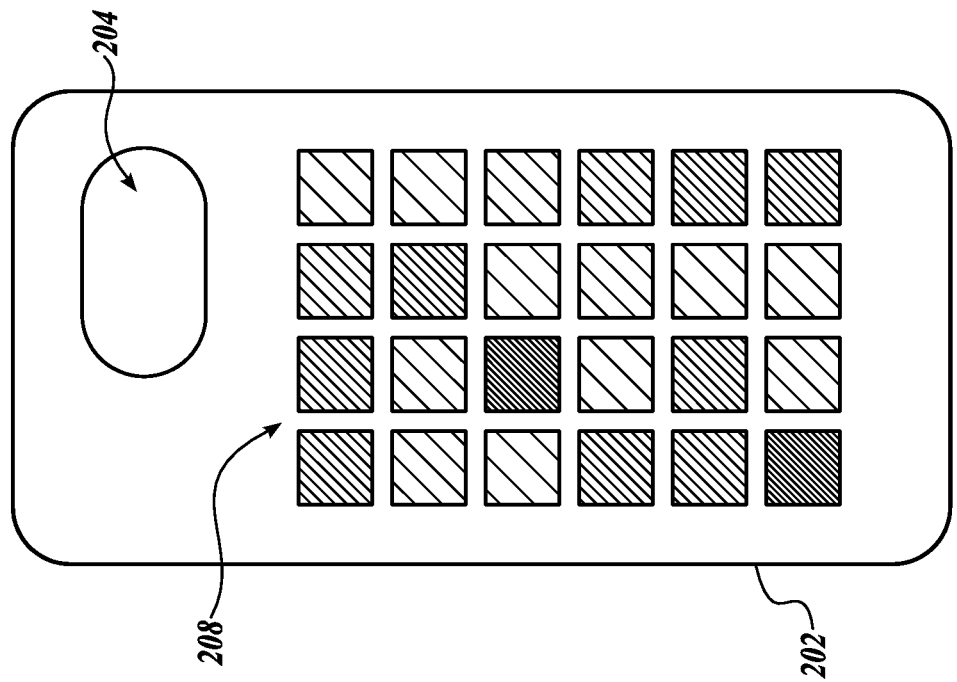
FIG. 2A and FIG. 2B are schematic drawings that illustrate a non-limiting example embodiment of a case for a smartphone computing device according to various aspects of the present disclosure.
Figure 2A:
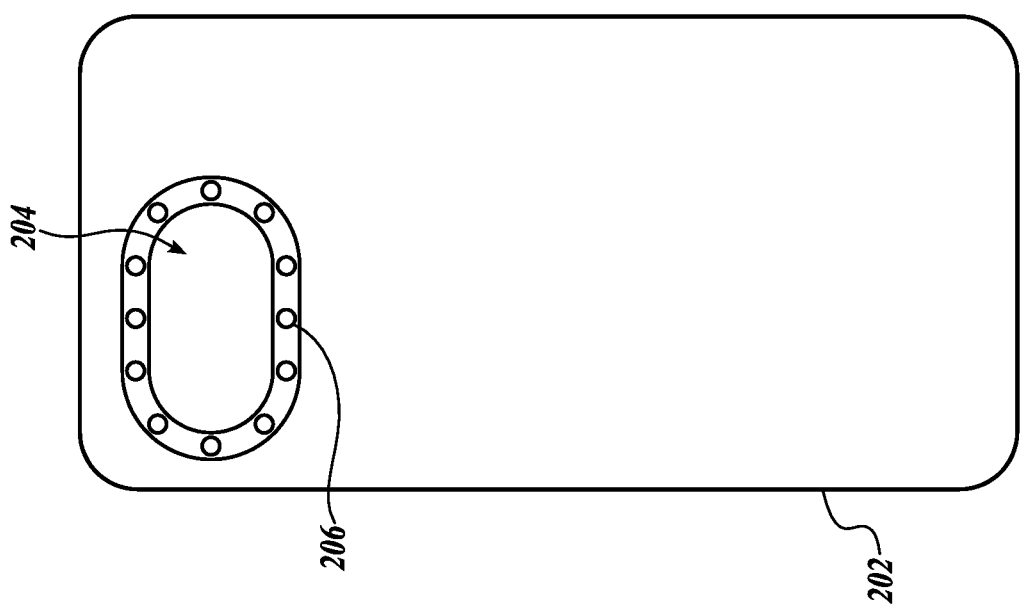

FIG. 2A and FIG. 2B are schematic drawings that illustrate a non-limiting example embodiment of a case for a smartphone computing device according to various aspects of the present disclosure. In FIG. 2A, an exterior portion of a smartphone case 202 is illustrated. The smartphone case 202 is configured to be attached to a smartphone computing device in order to protect the smartphone computing device from various types of physical damage. As shown, the smartphone case 202 includes an aperture 204 sized to avoid obscuring a low-dimensional color space camera and an illumination source of the smartphone computing device while the smartphone case 202 is attached to the smartphone computing device. The smartphone case 202 also includes a set of short-wavelength LEDs 206. By including short-wavelength LEDs 206 on the smartphone case 202, a smartphone computing device may be used to detect autofluorescence even if the smartphone computing device does not otherwise have a short-wavelength illumination source.

In FIG. 2B, an interior portion of a smartphone case 202 is illustrated. The aperture 204 is still visible in FIG. 2B, as is a color chart 208. The color chart 208 is provided on the smartphone case 202 so that any smartphone computing device that fits the smartphone case 202 may be calibrated using the same color chart 208, and the smartphone computing device may conveniently be recalibrated in different illumination conditions.

Figure 3:
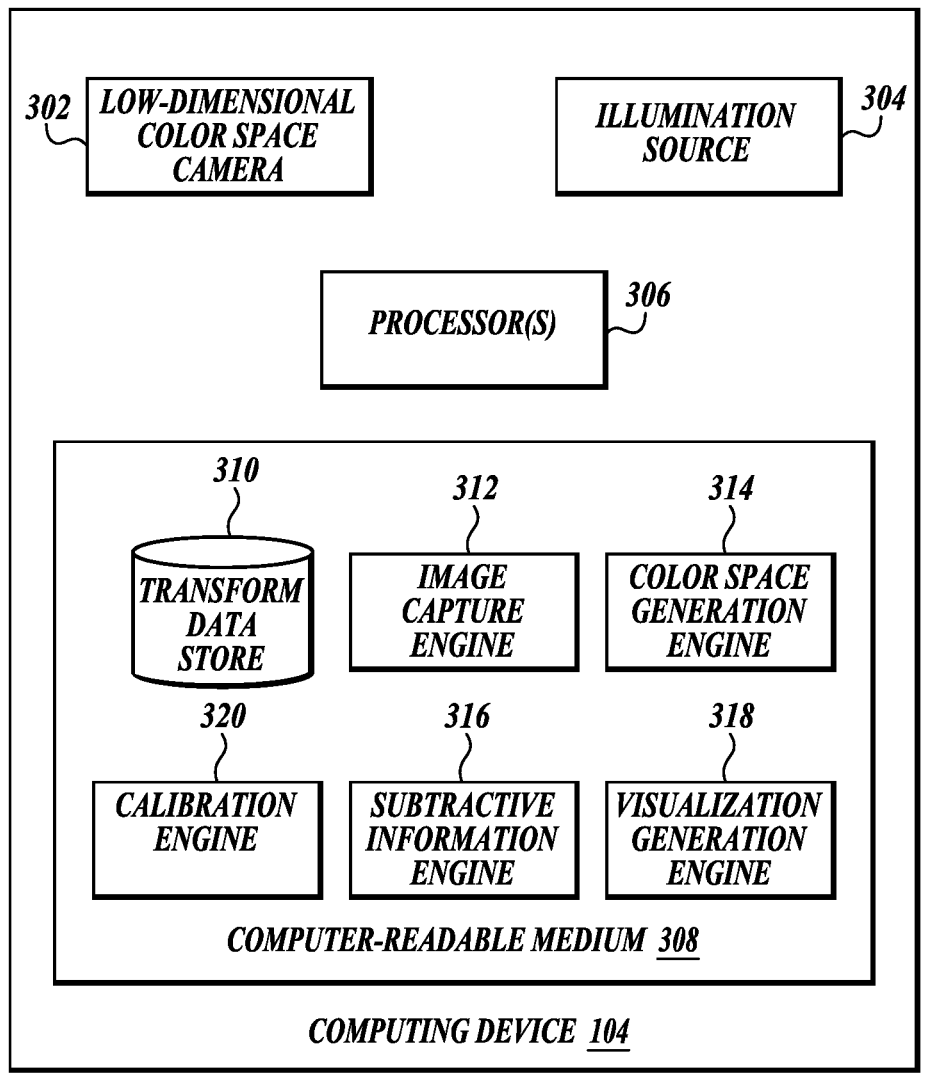
FIG. 3 is a block diagram that illustrates a non-limiting example embodiment of a computing device according to various aspects of the present disclosure.

FIG. 3 is a block diagram that illustrates a non-limiting example embodiment of a computing device according to various aspects of the present disclosure. As mentioned above, the computing device 104 may be a smartphone, or could be any other type of computing device with the illustrated components, including but not limited to a laptop computing device, a tablet computing device, a desktop computing device, or a kiosk.

In some embodiments, the components illustrated as part of the computing device 104 may be provided by more than one computing device. For example, one computing device may provide the low-dimensional color space camera 302 and the illumination source 304, while another computing device provides the processor(s) 306 and one or more of the components of the computer-readable medium 308. In one such embodiment, an image may be captured using the low-dimensional color space camera 302 and illumination source 304 of a first device, and the image may then be transmitted to a second computing device that provides the other components for further processing. As another example, the components of the computer-readable medium 308 may be provided by separate computing devices. For instance, one computing device (or collection of computing devices) may provide an image capture engine 312, a calibration engine 320, and a transform data store 310 for use in calibration, while another computing device (or collection of computing devices) may provide another transform data store 310, another image capture engine 312, a subtractive information engine 316, a color space generation engine 314, and a visualization generation engine 318 for generating visualizations. In some embodiments, some of the components illustrated as being present on the computer-readable medium 308 may be provided by a remote computing device including but not limited to one or more computing devices of a cloud computing system accessible via a network.

As shown in FIG. 3, the computing device 104 includes a low-dimensional color space camera 302, an illumination source 304, one or more processor(s) 306, and a computer-readable medium 308.

In some embodiments, the low-dimensional color space camera 302 is a camera of a smartphone, and is configured to capture information in a low-dimensional color space including but not limited to an RGB color space. Typically, the low-dimensional color space camera 302 is capable of capturing images in a relatively high resolution, such as 3264×2448 pixels. In other embodiments, any low-dimensional color space camera 302 capable of capturing images in a low-dimensional color space may be used.

In some embodiments, the illumination source 304 may be incorporated into the computing device 104, such as the flashlight of a smartphone. In some embodiments, the illumination source 304 may be separate from the computing device 104, such as overhead lighting or studio lighting. It has been determined that regular and consistent light sources other than a flashlight of a smartphone, such as a fluorescent lamp, may also be used as an illumination source 304.

In some embodiments, the processor(s) 306 include one or more general-purpose processors configured to execute instructions stored on the computer-readable medium 308. In some embodiments, the processor(s) 306 may include one or more special-purpose processors that are optimized for performing particular types of operations, including but not limited to specialized graphics processors (GPUs) and processors optimized for machine learning operations. In some embodiments, the computer-readable medium 308 may be any type of medium on which data and/or computer-executable instructions may be stored, including but not limited to flash memory, a magnetic disk such as a hard disk drive, an optical disk such as a CD-ROM or DVD-ROM, random access memory (RAM), or a read-only memory (ROM). In some embodiments, some aspects of the processor(s) 306 and/or the computer-readable medium 308 may be provided via specially configured hardware such as an ASIC or an FPGA.

As shown, the computer-readable medium 308 has stored thereon computer-executable instructions that, in response to execution by one or more of the processor(s) 306, cause the computing device 104 to provide a transform data store 310, a calibration engine 320, an image capture engine 312, a color space generation engine 314, a subtractive information engine 316, and a visualization generation engine 318.

In some embodiments, the calibration engine 320 is configured to use images captured by the high-dimensional color space camera 102 and the low-dimensional color space camera 302 to generate a transformation matrix, and to store the generated transformation matrix in the transform data store 310.

In some embodiments, the image capture engine 312 is configured to control the high-dimensional color space camera 102 and the low-dimensional color space camera 302 in order to collect calibration images, reference images, and input images for various purposes. In some embodiments, the image capture engine 312 may also be configured to control the illumination source 304. In some embodiments, the image capture engine 312 may not control the high-dimensional color space camera 102 and the low-dimensional color space camera 302, but may instead receive or retrieve images captured by those devices on their own.

In some embodiments, the color space generation engine 314 is configured to use a transformation matrix stored in the transform data store 310 to extract high-dimensional color space information from an image captured by the low-dimensional color space camera 302 that contains low-dimensional color space information. In some embodiments, the subtractive information engine 316 is configured to process high-dimensional color space information to emphasize the contribution of reflections from desired wavelength bands while minimizing contributions of reflections from undesired wavelength bands. In some embodiments, the visualization generation engine 318 is configured to generate visualizations of the emphasized wavelength bands, which may be useful for analyzing wavelength-dependent features of the target surface. Further details of each of these actions are described below.

Figure 4:
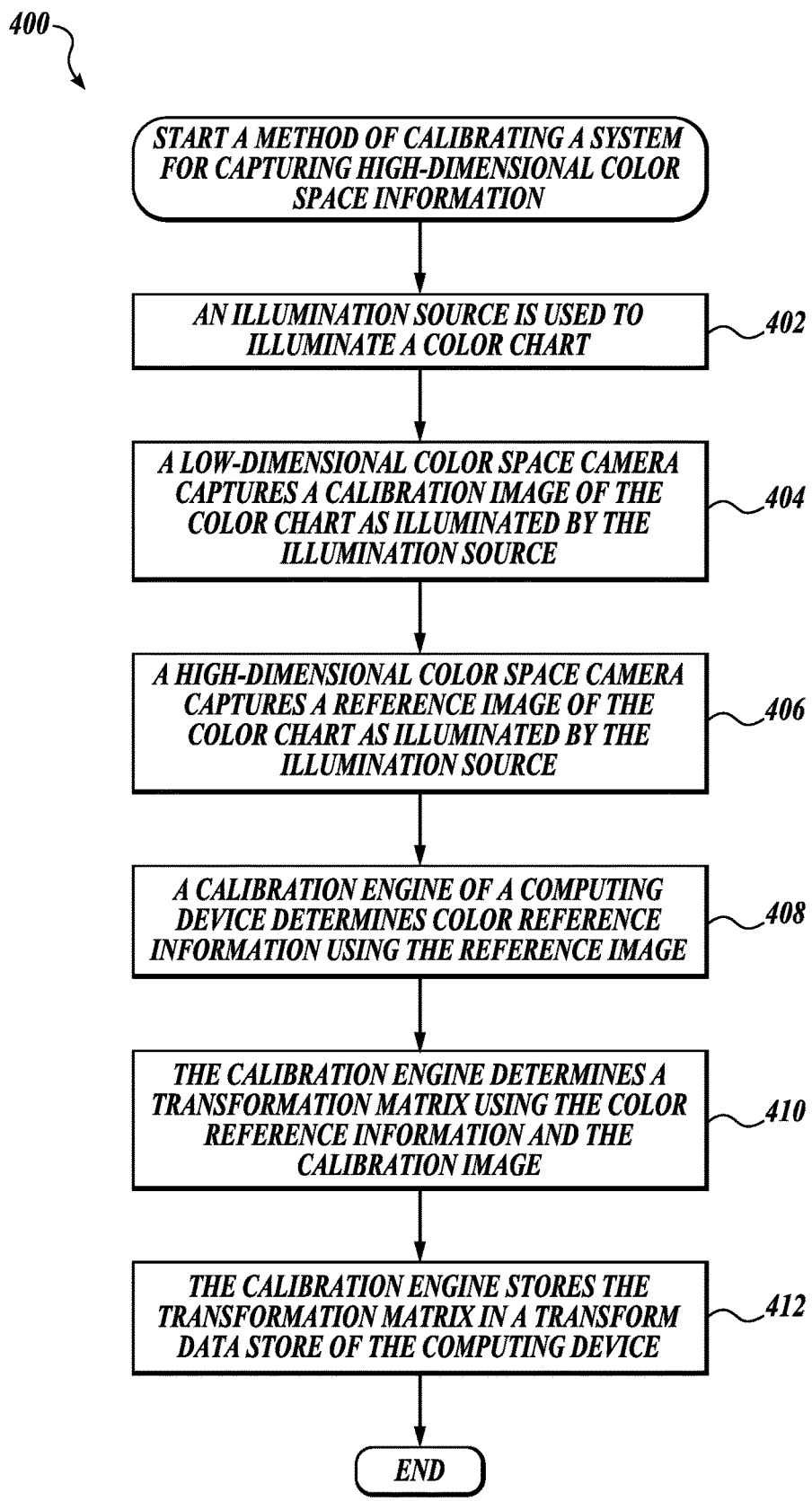
FIG. 4 is a flowchart that illustrates a non-limiting example embodiment of a method of calibrating a system for capturing high-dimensional color space information according to various aspects of the present disclosure.

FIG. 4 is a flowchart that illustrates a non-limiting example embodiment of a method of calibrating a system for capturing high-dimensional color space information according to various aspects of the present disclosure. The method 400 may performed at any time that a transformation matrix is needed. In some embodiments, the method 400 may be used to create a transformation matrix for each computing device 104 that will be used to generate visualizations as described below. In some embodiments, the method 400 may be used to create a transformation matrix for each model of computing device 104 that will be used to generate visualizations, with the assumption that any illumination source 304 and low-dimensional color space camera 302 in computing devices of matching models will also match, and so a transformation matrix created for one example of a model of a computing device 104 will be usable by any other example of the same model of the computing device 104 (e.g., a transformation matrix created using an iPhone 11 as the computing device 104 would work with any iPhone 11).

From a start block, the method 400 proceeds to block 402, where an illumination source 304 is used to illuminate a color chart 106. As discussed above, the illumination source 304 may be incorporated into the computing device 104, or may be separate from the computing device 104. Either way, it should be noted that the same illumination source 304 (or an illumination source 304 with matching spectral band characteristics) will be used during any method that consumes the transformation matrix determined by this method 400. In some embodiments, the room or other environment in which the color chart 106 is situated is kept dark other than the illumination source 304 so as to isolate reflections of the illumination source 304 from other ambient light sources of differing spectral characteristics.

At block 404, a low-dimensional color space camera 302 captures a calibration image of the color chart 106 as illuminated by the illumination source 304. The calibration image captured by the low-dimensional color space camera 302 includes low-dimensional color space information, such as RGB information split between a red band, a green band, and a blue band.

At block 406, a high-dimensional color space camera 102 captures a reference image of the color chart 106 as illuminated by the illumination source 304. The reference image captured by the high-dimensional color space camera 102 includes high-dimensional color space information, such as information separated into more than the three wavebands of the low-dimensional color space information. In one example embodiment, the high-dimensional color space information may be separated into 16 wavebands (also referred to herein as "subchannels"), though in other embodiments, more or fewer wavebands may be used. Typically, the reference image may have a lower resolution than the calibration image, though in some embodiments, the images may have matching resolutions.

At block 408, a calibration engine 320 of a computing device 104 determines color reference information using the reference image. The color reference information uses the wavelength band intensities detected by the high-dimensional color space camera 102 as the true wavelength band intensities reflected by the color chart 106. In some embodiments, only pixels that represent a center portion of each color box of the color chart 106 may be used so that precise detection of the edges of the color boxes is not necessary.

At block 410, the calibration engine 320 determines a transformation matrix using the color reference information and the calibration image. When a reference image is captured by the high-dimensional color space camera 102 and color reference information is extracted, the response of each subchannel of n subchannels is depicted as:

$$V'_c = \int l(\lambda)\gamma(\lambda)f_c(\lambda)s'(\lambda)d\lambda = \int m'_c(\lambda)\gamma(\lambda)d\lambda \qquad (1)$$

where $V'_{c'}$ is the response of c'th subchannel (c=1, 2, 3, ..., n), $f_{c'}(\lambda)$ is the spectral transmittance of the filter in c'th subchannel, s'(λ) is the spectral sensitivity. $m'_{c'}(\lambda)$ is the product of l(λ), $f_c(\lambda)$ and s(λ), which is the spectral responsivity of each subchannel in the high-dimensional color space camera 102. The matrix form of equation (1) is then expressed as:

$$V' = M'\gamma \qquad (2)$$

where V' is the vector of hyperspectral camera response, M' is the matrix of spectral responsivity in the high-dimensional color space camera 102. To reconstruct high-dimensional color space information from low-dimensional color space information, we assume the reconstruction matrix is W. The process is expressed as:

$$\tilde{V}' = WV \qquad (3)$$

where $\tilde{V}'$ is the reconstructed image having high-dimensional color space information. To ensure the accuracy of reconstruction, the minimum square error between the reconstructed high-dimensional color space information and the original reference image should be minimized. The minimum square error is calculated as:

$$e = \langle (V'-\tilde{V}')^t(V'-\tilde{V}') \rangle = \langle V'^t V' \rangle - W^t \langle V'^t V' \rangle - W^t \langle V'^t V' \rangle \\ + W^t W \langle V'^t V' \rangle \qquad (6)$$

When the partial derivative of e with respect to W is zero, the minimum square error is minimized, expressed as:

$$\frac{\partial e}{\partial W} = -\langle V'^t V \rangle + W^t \langle V^t V \rangle = 0 \qquad (4)$$

The transformation matrix is derived as:

$$W = \langle V'V^t \rangle \langle VV^t \rangle^{-1} \qquad (5)$$

where W is an ensemble-averaging operator, $\langle V'V^t \rangle$ is the correlation matrix between the hyperspectral response and low-dimensional color space camera response, and $\langle VV^t \rangle$ is the autocorrelation matrix of the low-dimensional color space camera response.

At block 412, the calibration engine 320 stores the transformation matrix in a transform data store 310 of the computing device 104. In some embodiments, the transform data store 310 may be on the same computing device 104 as the calibration engine 320. In some embodiments, the transform data store 310 may be on a different computing device 104, such as in embodiments wherein a first computing device 104 is used to generate the transformation matrix, and that transformation matrix is then provided for use by other computing devices that match the computing device 104.

The method 400 then proceeds to an end block and terminates. One will note that though the method 400 describes the convenient use of a high-dimensional color space camera 102 to capture a reference image and extract color reference information in block 406 to block 408, other techniques for extracting the color reference information may be used. For example, in some embodiments, a spectrometer may be used to measure the color chart 106 and determine the color reference information. As another example, in some embodiments, known color values may be used to create the color chart 106, and color reference information may be directly generated from the specification of the color chart 106.

Figure 5:
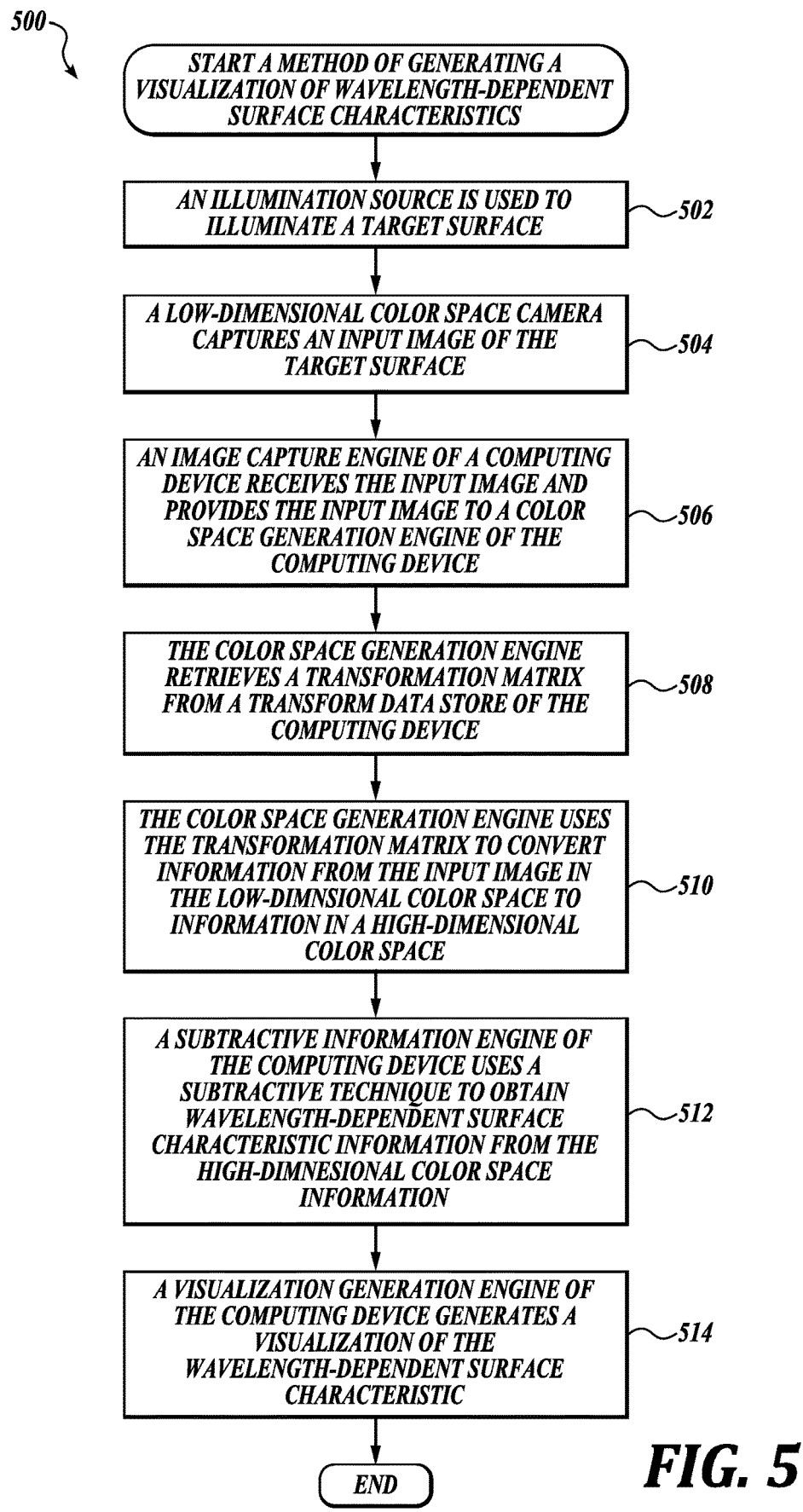
FIG. 5 is a flowchart that illustrates a non-limiting example embodiment of a method of generating a visualization of wavelength-dependent surface characteristics according to various aspects of the present disclosure.

FIG. 5 is a flowchart that illustrates a non-limiting example embodiment of a method of generating a visualization of wavelength-dependent surface characteristics according to various aspects of the present disclosure.

From a start block, the method 500 proceeds to block 502, where an illumination source 304 is used to illuminate a target surface. In some embodiments, the target surface may be an area of skin of a subject. Some embodiments of the present disclosure may be particularly suited for skin as a target surface, since reflectance of various components of skin (such as hemoglobin and melanin) varies by wavelength, and so the method 500 can be used to separately visualize these components. However, these examples should not be seen as limiting, and some embodiments of method 500 may be used to visualize wavelength-dependent surface features on other types of target surfaces.

The illumination source 304 matches the illumination source 304 used in method 400 during creation of the transformation matrix. In some embodiments, the illumination source 304 used at block 502 may be the same device used as the illumination source 304 in method 400. In some embodiments, the illumination source 304 used in block 502 may be a different device that nevertheless has spectral wavelength characteristics that match those of the illumination source 304 used in method 400. In some embodiments, the target surface and illumination source 304 may be positioned in an otherwise dark environment so that an affect of ambient light from sources other than the illumination source 304 is minimized.

At block 504, a low-dimensional color space camera 302 captures an input image of the target surface. In some embodiments, the low-dimensional color space camera 302 may be operated to capture the input image by the image capture engine 312. In some embodiments, the low-dimensional color space camera 302 may be operated manually by a user of the computing device 104 to capture the input image.

At block 506, an image capture engine 312 of a computing device 104 receives the input image and provides the input image to a color space generation engine 314 of the computing device 104. At block 508, the color space generation engine 314 retrieves a transformation matrix from a transform data store 310 of the computing device 104. The transformation matrix is the transformation matrix that was generated for the low-dimensional color space camera 302 and the illumination source 304 using method 400. At block 510, the color space generation engine 314 uses the transformation matrix as described above to convert information from the input image in the low-dimensional color space to information in a high-dimensional color space.

At block 512, a subtractive information engine 316 of the computing device 104 uses a subtractive technique to obtain wavelength-dependent surface characteristic information from the high-dimensional color space information. By using a weighted subtraction technique, absorption caused by a first wavelength-dependent characteristic can be minimized while absorption caused by a second wavelength-dependent characteristic can be emphasized, thus allowing visualizations of the second characteristic.

The weighted subtraction is expressed as:

$$C_r = C_1 - KC_2 = mx_1l_1 + ny_1l_1 - K(mx_2l_2 + ny_2l_2) = m(x_1l_1 - Kx_2l_2) + n(y_1l_1 - Ky_2l_2) \quad (6)$$

where $C_r$ is the estimated reflection of the target surface that is assumed to be influenced by the absorption of the first characteristic and the second characteristic, $C_1$ and $C_2$ are the detected reflections at two selected wavebands. K represents the ratio of weighted subtraction. m and n are the concentrations of the first characteristic and the second characteristic in the target surface. $l_1$ and $l_2$ are the illumination intensity at two selected wavebands. $x_1$ and $x_2$ are the reflectance of the first characteristic at two selected wavebands. $y_1$ and $y_2$ are the reflectance of the second characteristic at two selected wavebands. By setting the value of K to be $$\frac{y_1 l_1}{y_2 l_2},$$

the reflection of the first characteristic in the data can be extracted via the simplified equation:

$$m = \frac{C_r}{\left(x_1 l_1 - \frac{y_1 l_1 \cdot x_2 l_2}{y_2 l_2}\right)} \quad (7)$$

For example, values of absorption caused by hemoglobin in blood may be subtracted from values of absorption caused by melanin in order to emphasize the melanin concentrations in various areas of skin. As another example, values of absorption caused by melanin may be subtracted from values of absorption caused by hemoglobin in order to show blood perfusion, or from values of oxyhemoglobin and deoxyhemoglobin in order to visualize circulation. In one example where hemoglobin was used as the first characteristic and melanin was used as the second characteristic, several red light wavebands, including 615 nm, 625 nm, 603 nm, and 595 nm were selected and subtracted one by one from green light wavebands, including 556 nm, 544 nm, 529 nm, and 543 nm. This weighted subtraction minimized or eliminated the melanin absorption to emphasize the hemoglobin absorption, thus showing blood perfusion in the target surface. By conducting similar weighted subtraction processing between blue light wavebands (582 nm, 494 nm, 472 nm, and 465 nm) and the green light wavebands, the superficial melanin can be emphasized. Likewise, by conducting similar weighted subtraction processing between 600 nm and 560 nm, autofluorescence of porphyrin-producing bacteria can be emphasized compared to background autofluorescence.

Figure 6:
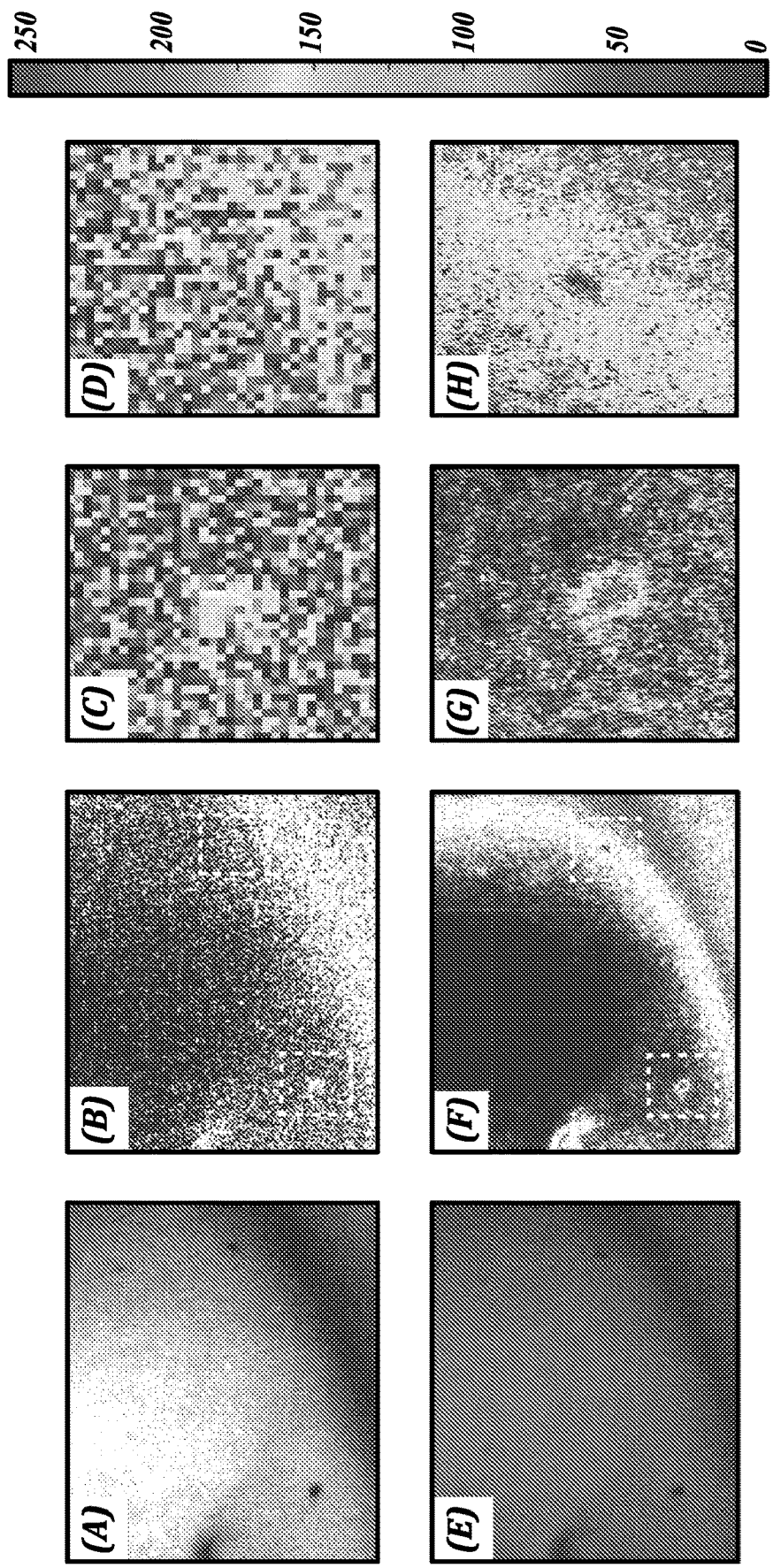
FIG. 6 illustrates results of a skin analysis performed with a high-dimensional color space camera versus a computing device according to various aspects of the present disclosure.

At block 514, a visualization generation engine 318 of the computing device 104 generates a visualization of the wavelength-dependent surface characteristic. In some embodiments, the visualization may be an image that includes the reflection values as updated by the weighted subtraction process. In some embodiments, the visualization may be an image with data limited to the wavelengths of interest, as updated by the weighted subtraction. Some examples of visualizations are illustrated in FIG. 6 and described below.

The method 500 then proceeds to an end block and terminates.

Method 500 describes emphasizing a single surface characteristic. In some embodiments, multiple characteristics may be analyzed. For example, in one real-time monitoring experiment, hemoglobin absorption information was extracted from hyperspectral images reconstructed from RGB-image sequences and quantitatively analyzed the skin hemodynamics during heartbeat cycle and vascular occlusion. Furthermore, in the monitoring to vascular occlusion, besides the blood absorption, oxygen saturation (SaO2) was also estimated. In this case, oxyhemoglobin and deoxyhemoglobin are studied independently. The reflection is expressed as:

$$C_i = m_{oxy} x_i^{oxy} + m_{deo} x_i^{deo} + \alpha \quad (8)$$

where $C_i$ is the detected reflection at the selected wavebands, $m_{oxy}$ and $m_{deo}$ are the concentrations of oxy and deoxyhemoglobin, respectively, $x_i^{oxy}$ and $x_i^{deo}$ are the corresponding reflectance coefficients of oxyhemoglobin and deoxyhemoglobin, and $\alpha$ is a term that represents the light intensity losses caused by other chromophores, including melanin. Bands 4 (570 nm), 5 (581 nm) and 6 (556 nm) were selected for the evaluation of SaO2. Since the sensitive wavelengths in these bands are close to each other, it may be assumed that is a constant in the processing. From equation (8), the $SaO_2$ can be evaluated as:

$$SaO_2 = \frac{m_{oxy}}{(m_{oxy} + m_{deo})} \quad (9)$$

To investigate the reconstruction performance, RGB images of 100 color blocks were reconstructed from the color chart into hyperspectral images with a Wiener estimation matrix. For each color block, the average value of relative errors of 16 subchannels were between initial and reconstructed hyperspectral reflectance were calculated. The maximum, minimum and average values of the averaged relative errors of 100 color blocks are 10.950%, 0.424% and 4.933%, respectively. Relative errors of the reconstruction are higher in some color blocks that were mainly with dark cold tone, which coincides with the lower spectral intensity at the band around 500 nm. To show the reconstruction in more detail, 6 samples were randomly selected and compared regarding their initial and reconstructed reflectance in 16 wavebands. The results indicate that reconstructed hyperspectral images from RGB images match well with the initial hyperspectral images.

FIG. 6 illustrates results of a skin analysis performed with a high-dimensional color space camera 102 versus a computing device 104 according to various aspects of the present disclosure. To compare the skin analysis performance of the RGB-camera-based hyperspectral imaging system and snapshot hyperspectral camera, the same skin area was imaged with two cameras and conducted via the same process. Melanin absorption information was extracted and compared as an example. FIG. 6(a) shows the raw image from the band 9 in the snapshot hyperspectral camera. The extracted melanin absorption map from the images captured by hyperspectral camera is shown in FIG. 6(b), where the details of two melanocytic nevi (marked by square boxes) are shown in the zoomed-in images (FIG. 6(c, d)). Analyses of the images captured by the smartphone resulted in melanin absorption map shown in FIG. 6(f). FIG. 6(g) and FIG. 6(h) are the zoomed-in view of the two melanocytic nevus, marked by square boxes in FIG. 6(f). Since the smartphone camera has much more pixels than the snapshot camera, the melanin absorption map in FIG. 6(f) performs much better in terms of image resolution. From the zoomed-in images, we can see that two melanocytic nevus absorption spots from smartphone-based system (FIG. 6(g, h)) show clear edges and sizes. However, these characteristics are not clearly depicted by the snapshot hyperspectral camera largely due to its limited spatial resolution.

In some embodiments, characteristics other than melanin and hemoglobin may be analyzed. Indeed, any characteristic for which spectral characteristics differ may be analyzed. For example, the recent developments of fluorescence imaging have presented new interests and opportunities for assessing bacteria contents in human tissue. Porphyrins, for example, as the byproducts of bacterial reproduction and metabolism accumulating in sebaceous glands in skin and dental plaque, fluoresce red light signals under black light stimulation, which can be contrasted from green autofluorescence background (originated from endogenous tissue). By tracking porphyrins-induced red fluorescence signals, the bacteria-contaminated human tissue can be effectively mapped. To detect autofluorescence, an illumination source 304 that includes black light LEDs (365 nm) may be used, and a fluorescence color chart 106 may be used, such as a paper stained with various colors of black light fluorescent dyes used for body paint, mixed to create 40 different color blocks. This illumination source 304 and color chart 106 may be used to create a transformation matrix with 15 wavebands In some embodiments, a computing device 104 calibrated using a visible light illumination source may be used to make measurements with a short-wavelength illumination source 304 in order to cause autofluorescence in the calibrated wavelength ranges.

Once the transformation matrix is created and an input image is captured, the weighted subtraction may be used to emphasize porphyrin-related autofluorescence of bacteria from the background autofluorescence in order to generate a visualization. For emphasizing porphyrin-related autofluorescence compared to background autofluorescence from skin, we selected 600 nm and 560 nm as two wavebands to conduct dual-waveband processing as described above, and used a subtraction ratio of 1.22. We found that the autofluorescence signals from the background skin tissue were greatly decreased so that porphyrins were contrasted. For emphasizing porphyrin-related autofluorescence compared to background autofluorescence from teeth, we used the same wavebands, but used a weighted subtraction ratio of 0.58. We found that by using the techniques described herein, the bacteria-related features were enhanced between 5 to 15 times, thus allowing a clear visualization of the bacteria-related features to be generated.

Figure 7:
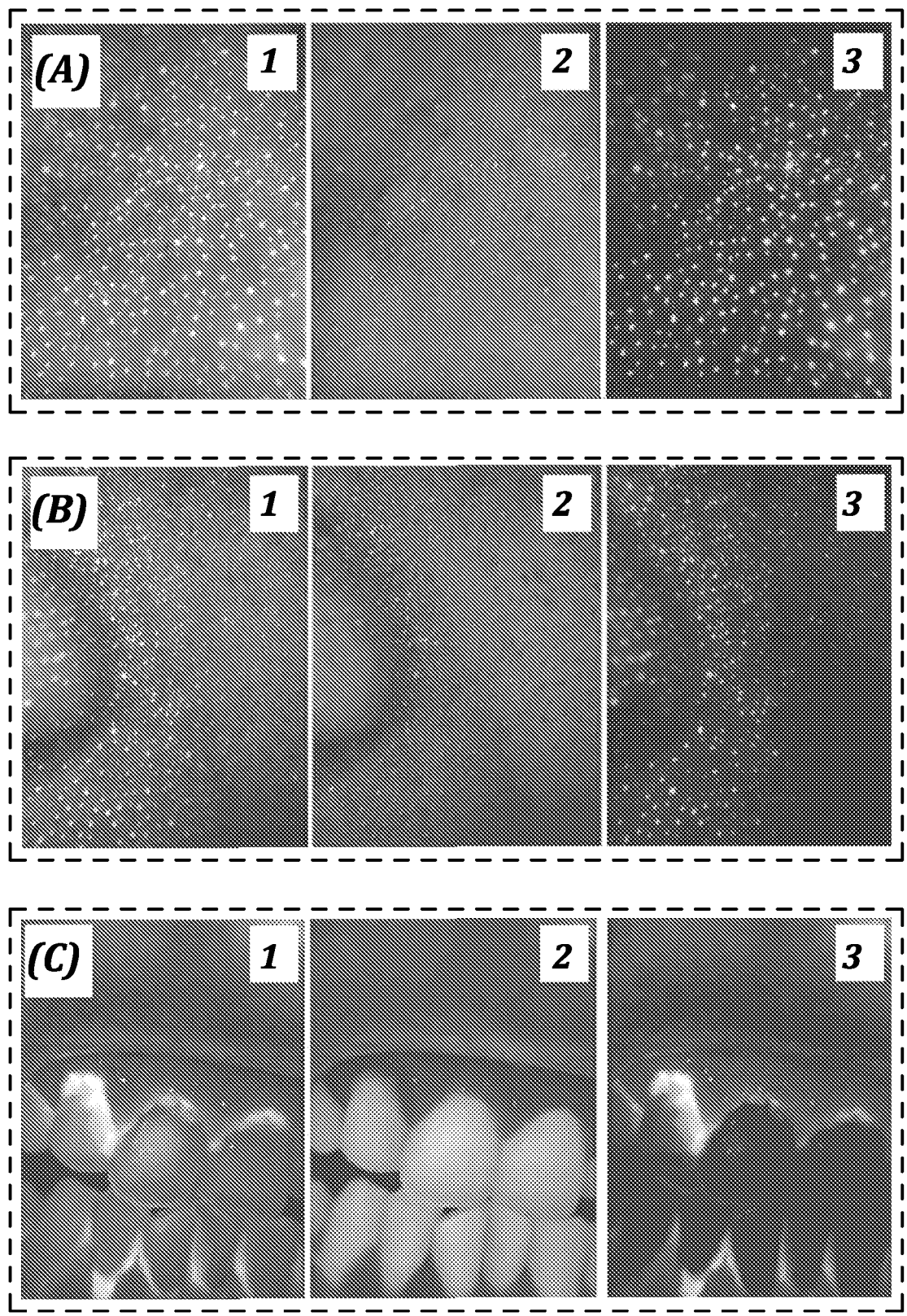
FIG. 7 shows results of using the techniques described above to extract and visualize autofluorescence information according to various aspects of the present disclosure.

FIG. 7 shows results of using the techniques described above to extract and visualize autofluorescence information according to various aspects of the present disclosure. Images (A1), (B1), and (C1) illustrate visualization of the background information from the 600 nm waveband. Images (A2), (B2), and (C2) illustrate visualization of the autofluorescence information from the 560 nm waveband. Images (A3), (B3), and (C3) illustrate the background-eliminated, bacteria-targeted feature mapping.

Figure 8:
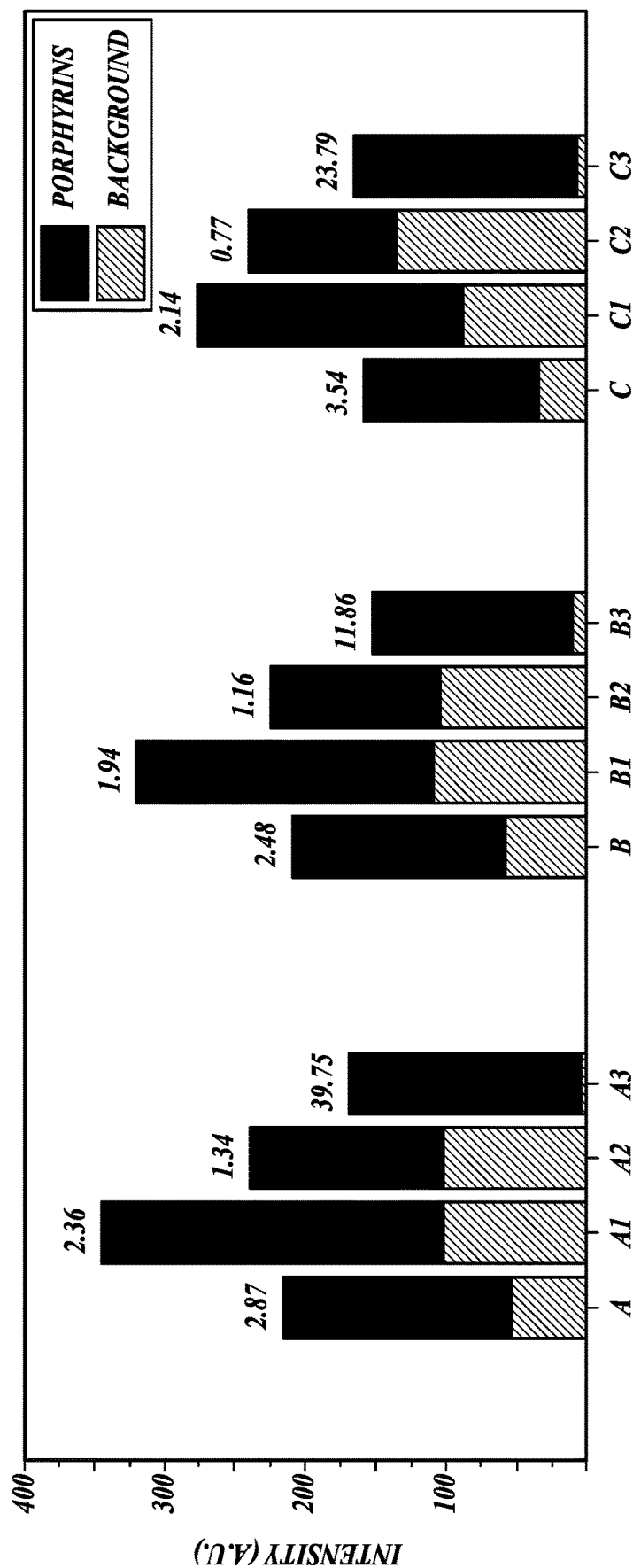
FIG. 8 illustrates a quantitative analysis of the effectiveness of these techniques of extracting information representing bacteria-produced porphyrins from background autofluorescence.

It is clear from the difference between the (1) images and the (3) images that the techniques described above provide a clear visualization of the autofluorescence information with the background information minimized. FIG. 8 illustrates a quantitative analysis of the effectiveness of these techniques of extracting information representing bacteria-produced porphyrins from background autofluorescence. The labeled numbers on the histogram are intensity ratios between porphyrin signals and background signals. The bars for (A), (B), and (C) show the unprocessed images, and the bars for (A1) through (C3) correspond to the images in FIG. 7. As shown, the intensity ratios for the processed images are remarkably greater than the other images.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

As used herein and unless otherwise indicated, the terms "a" and "an" are taken to mean "one", "at least one" or "one or more". Unless otherwise required by context, singular terms used herein shall include pluralities and plural terms shall include the singular.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

All of the references cited herein are incorporated by reference. Aspects of the disclosure can be modified, if necessary, to employ the systems, functions, and concepts of the above references and application to provide yet further embodiments of the disclosure. These and other changes can be made to the disclosure in light of the detailed description.

Specific elements of any foregoing embodiments can be combined or substituted for elements in other embodiments. Moreover, the inclusion of specific elements in at least some of these embodiments may be optional, wherein further embodiments may include one or more embodiments that specifically exclude one or more of these specific elements. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

Example devices, methods, and systems are described herein. It should be understood the words "example," "exemplary," and "illustrative" are used herein to mean "serving as an example, instance, or illustration." Any embodiment or feature described herein as being an "example," being "exemplary," or being "illustrative" is not necessarily to be construed as preferred or advantageous over other embodiments or features. The example embodiments described herein are not meant to be limiting. It will be readily understood aspects of the present disclosure, as generally described herein, and illustrated in the figures, can be arranged, substituted, combined, separated, and designed in a wide variety of different configurations, all of which are explicitly contemplated herein.

Furthermore, the particular arrangements shown in the Figures should not be viewed as limiting. It should be understood other embodiments may include more or less of each element shown in a given Figure. Further, some of the illustrated elements may be combined or omitted. Yet further, an example embodiment may include elements not illustrated in the Figures. As used herein and unless stated otherwise, "about" means +/−5% of the stated amount.

The embodiments of the invention in which an exclusive property or privilege is claimed are defined as follows:

1. A computer-implemented method of generating a visualization of wavelength-dependent surface characteristics, the method comprising:
   receiving, by a computing device, an input image captured by a camera, wherein the input image includes information in a low-dimensional color space;
   processing, by the computing device, the input image to determine spectrum band information in a high-dimensional color space that corresponds to the input image;
   extracting, by the computing device, subtractive information representing a contribution of a background characteristic from the spectrum band information to obtain wavelength-dependent surface characteristic information representing a target characteristic; and
   generating, by the computing device, the visualization using the wavelength-dependent surface characteristic information;
   wherein extracting subtractive information includes:
   multiplying a detected reflectance by a ratio that represents a proportion of reflectance caused by the target characteristic and the background characteristic in a first set of wavelength bands compared to a second set of wavelength bands.

2. The method of claim 1, wherein the low-dimensional color space has three spectrum bands, and wherein the high-dimensional color space includes more than three spectrum bands.

3. The method of claim 1, wherein processing the input image to determine spectrum band information in the high-dimensional color space that corresponds to the input image includes:
   transforming the information in the low-dimensional color space into the information in the high-dimensional color space using a transformation matrix.

4. The method of claim 1, wherein the target characteristic is melanin concentration, wherein the background characteristic is hemoglobin concentration, and wherein generating the visualization using the wavelength-dependent surface characteristic information includes generating a visualization of melanin concentration.

5. The method of claim 1, wherein the target characteristic is hemoglobin concentration, wherein the background characteristic is melanin concentration, and wherein generating the visualization using the wavelength-dependent surface characteristic information includes generating a visualization of hemoglobin concentration.

6. The method of claim 1, wherein the target characteristic is autofluorescence of bacteria-produced porphyrins, wherein the background characteristic is autofluorescence of facial skin or teeth, and wherein generating the visualization using the wavelength-dependent surface characteristic information includes generating a visualization of bacteria-produced porphyrins.

7. A system, comprising:
   a low-dimensional color space camera;
   an illumination source; and
   a non-transitory computer-readable medium having computer-executable instructions stored thereon that, in response to execution by one or more processors of the system, cause the system to perform actions comprising:
   receiving an input image of a target surface captured using the low-dimensional color space camera and illuminated using the illumination source;

processing the input image to determine spectrum band information in a high-dimensional color space that corresponds to the input image;

extracting subtractive information representing a contribution of a background characteristic from the spectrum band information to obtain wavelength-dependent surface characteristic information representing a target characteristic; and generating a visualization of a wavelength-dependent surface characteristic using the wavelength-dependent surface characteristic information;

wherein extracting the subtractive information representing the contribution of the background characteristic from the spectrum band information to obtain wavelength-dependent surface characteristic information representing the target characteristic includes multiplying a detected reflectance by a ratio that represents a proportion of reflectance caused by the target characteristic and the background characteristic in a first set of wavelength bands compared to a second set of wavelength bands.

8. The system of claim 7, further comprising a smartphone that includes at least the low-dimensional color space camera and the illumination source.

9. The system of claim 7, wherein processing the input image to determine spectrum band information in the high-dimensional color space that corresponds to the input image includes:
transforming the input image from the low-dimensional color space to the high-dimensional color space using a transformation matrix.

10. The system of claim 7, wherein the target characteristic is melanin concentration, wherein the background characteristic is hemoglobin concentration, and wherein generating the visualization using the wavelength-dependent surface characteristic information includes generating a visualization of melanin concentration.

11. The system of claim 7, wherein the target characteristic is hemoglobin concentration, wherein the background characteristic is melanin concentration, and wherein generating the visualization using the wavelength-dependent surface characteristic information includes generating a visualization of hemoglobin concentration.

12. The system of claim 7, wherein the target characteristic is autofluorescence of bacteria-produced porphyrins, wherein the background characteristic is autofluorescence of facial skin or teeth, and wherein generating the visualization using the wavelength-dependent surface characteristic information includes generating a visualization of bacteria-produced porphyrins.

13. A non-transitory computer-readable medium having computer-executable instructions stored thereon that, in response to execution by one or more processors of a computing device, cause the computing device to perform actions for generating a visualization of wavelength-dependent surface characteristics, the actions comprising:
receiving, by the computing device, an input image captured by a camera, wherein the input image includes information in a low-dimensional color space;

processing, by the computing device, the input image to determine spectrum band information in a high-dimensional color space that corresponds to the input image;

extracting, by the computing device, subtractive information representing a contribution of a background characteristic from the spectrum band information to obtain wavelength-dependent surface characteristic information representing a target characteristic; and generating, by the computing device, the visualization using the wavelength-dependent surface characteristic information;

wherein extracting subtractive information includes multiplying a detected reflectance by a ratio that represents a proportion of reflectance caused by the target characteristic and the background characteristic in a first set of wavelength bands compared to a second set of wavelength bands.

14. The non-transitory computer-readable medium of claim 13, wherein the target characteristic is melanin concentration, wherein the background characteristic is hemoglobin concentration, and wherein generating the visualization using the wavelength-dependent surface characteristic information includes generating a visualization of melanin concentration.

15. The non-transitory computer-readable medium of claim 13, wherein the target characteristic is hemoglobin concentration, wherein the background characteristic is melanin concentration, and wherein generating the visualization using the wavelength-dependent surface characteristic information includes generating a visualization of hemoglobin concentration.

16. The non-transitory computer-readable medium of claim 13, wherein the target characteristic is autofluorescence of bacteria-produced porphyrins, wherein the background characteristic is autofluorescence of facial skin or teeth, and wherein generating the visualization using the wavelength-dependent surface characteristic information includes generating a visualization of bacteria-produced porphyrins.

17. The non-transitory computer-readable medium of claim 13, wherein processing the input image to determine spectrum band information in the high-dimensional color space that corresponds to the input image includes:
transforming the information in the low-dimensional color space into the information in the high-dimensional color space using a transformation matrix.

18. The system of claim 7, further comprising a first device and a second device separate from the first device;
wherein the first device includes the low-dimensional color space camera and the illumination source; and
wherein the second device includes the one or more processors of the system.

19. The system of claim 7, wherein the actions further comprise:
illuminating the target surface using the illumination source; and
capturing the input image of the target surface using the low-dimensional color space camera.

* * * * *